United States Patent [19]
Crawford et al.

[11] Patent Number: 5,881,122
[45] Date of Patent: Mar. 9, 1999

[54] COMPUTED TOMOGRAPHY SCANNING APPARATUS AND METHOD FOR GENERATING PARALLEL PROJECTIONS USING NON-PARALLEL SLICE DATA

[75] Inventors: Carl R. Crawford, Brookline; Christopher C. Ruth, Danvers, both of Mass.

[73] Assignee: Analogic Corporation, Peabody, Mass.

[21] Appl. No.: 948,492

[22] Filed: Oct. 10, 1997

Related U.S. Application Data

[63] Continuation-in-part of Ser. No. 831,558, Apr. 9, 1997, Pat. No. 5,802,134.

[51] Int. Cl.⁶ .................................................. A61B 6/03
[52] U.S. Cl. ................. 378/4; 378/15; 378/901
[58] Field of Search .................. 378/4, 15, 901; 250/363.02, 363.04, 363.1, 370.08, 370.09, 370.1

[56] References Cited

U.S. PATENT DOCUMENTS

| | | | |
|---|---|---|---|
| 5,414,622 | 5/1995 | Walters | 382/131 |
| 5,802,134 | 1/1998 | Larson et al. | 378/4 |

*Primary Examiner*—David P. Porta
*Assistant Examiner*—David Vernon Bruce
*Attorney, Agent, or Firm*—Lappin & Kusmer

[57] ABSTRACT

A nutating slice CT image reconstruction apparatus and method generates a set of projection data using helical cone-beam scanning. The three-dimensional projection data is used to reconstruct a series of planar image slices. The slices are selected such that they define a tilt angle and a rotation angle with respect to the longitudinal axes of the object being scanned. Successive slices have equal tilt angles but changing rotation angles such that normal axes of successive slices define a nutation and precession about the longitudinal axis of the object. Projection data for the tilted slices are formed of selected one-dimensional fan-beam data. As such, the projection data can be applied to conventional two-dimensional reconstruction approaches to generate an image. The projection data can also be used to generate two-dimensional projection images at one or more stationary projection angles through an object being scanned. The nutation or tilt of image volume elements can be compensated for to provide a more accurate image and more accurate target assessment such as accurate total mass determination. A parallel processing architecture can be used to generate and process the nutated slices with improved efficiency.

22 Claims, 14 Drawing Sheets

COMPUTED TOMOGRAPHY SCANNING APPARATUS AND METHOD FOR GENERATING PARALLEL PROJECTIONS USING NON-PARALLEL SLICE DATA

RELATED APPLICATIONS

This application is a continuation-in-part of U.S. application Ser. No. 08/831,558, filed on Apr. 9, 1997, now U.S. Pat. No. 5,802,134 of common assignee, the contents of which are incorporated herein in their entirety by reference.

This application is related to the following U.S. applications filed on even date herewith, of common assignee, the contents of which are incorporated herein in their entirety by reference:

"Computed Tomography Scanner Drive System and Bearing," invented by Andrew P. Tybinkowski, et al., U.S. Ser. No. 08/948,930;

"Air Calibration Scan for Computed Tomography Scanner with Obstructing Objects," invented by David A. Schafer, et al., U.S. Ser. No. 08/948,937;

"Computed Tomography Scanning Apparatus and Method With Temperature Compensation for Dark Current Offsets," invented by Christopher C. Ruth, et al., U.S. Ser. No. 08/948,928;

"Computed Tomography Scanning Target Detection Using Non-Parallel Slices," invented by Christopher C. Ruth, et al., U.S. Ser. No. 08/948,491;

"Computed Tomography Scanning Target Detection Using Target Surface Normals," invented by Christopher C. Ruth, et al., U.S. Ser. No. 08/948,929;

"Parallel Processing Architecture for Computed Tomography Scanning System Using Non-Parallel Slices," invented by Christopher C. Ruth, et al., U.S. Ser. No. 08/948,697;

"Computed Tomography Scanning Apparatus and Method Using Adaptive Reconstruction Window," invented by Bernard M. Gordon, et al., U.S. Ser. No. 08/949,127;

"Area Detector Array for Computed Tomography Scanning System," invented by David A Schafer, et al., U.S. Ser. No. 08/948,450;

"Closed Loop Air Conditioning System for a Computed Tomography Scanner," invented by Eric Bailey, et al., U.S. Ser. No. 08/948,692;

"Measurement and Control System for Controlling System Functions as a Function of Rotational Parameters of a Rotating Device," invented by Geoffrey A. Legg, et al., U.S. Ser. No. 08/948,493;

"Rotary Energy Shield for Computed Tomography Scanner," invented by Andrew P. Tybinkowski, et al., U.S. Ser. No. 08/948,698.

FIELD OF THE INVENTION

The present invention relates generally to computed tomography (CT) imaging and more particularly to CT imaging with improved efficiency and reduced image artifacts.

BACKGROUND OF THE INVENTION

FIG. 1 is a schematic axial view of a typical conventional CT scanner 10 which includes an x-ray source 12 and an x-ray detector system 14 secured to diametrically opposite sides of an annular shaped disk 16. The disk 16 is rotatably mounted within a gantry support (not shown), so that during a scan the disk 16 continuously rotates about a z-axis while x-rays pass from the source 12 through an object, such as a patient 20 positioned on a patient table 56 within the opening of the disk 16. The z-axis is normal to the plane of the page in FIG. 1 and intersects the scanning plane at the mechanical center of rotation 18 of the disk 16. The mechanical center of rotation 18 of the disk corresponds to the "isocenter" of the reconstructed image.

In one conventional system, the detector system 14 includes an array of individual detectors 22 disposed in a single row in a shape of an arc having a center of curvature at the point 24, referred to as the "focal spot," where the radiation emanates from the x-ray source 12. The source 12 and array of detectors 22 are positioned so that the x-ray paths between the source and each detector all lie in a "scanning plane" that is normal to the z-axis. Since the x-ray paths originate from what is substantially a point source and extend at different angles to the detectors, the x-ray paths form a "fan beam" 26 that is incident on the detector array 14 in the form of one-dimensional linear projection. The x-rays incident on a single detector at a measuring instant during a scan are commonly referred to as a "ray," and each detector generates an output signal indicative of the intensity of its corresponding ray. Since each ray is partially attenuated by all the mass in its path, the output signal generated by each detector is representative of the attenuation of all the mass disposed between that detector and the X-ray source, i.e., the attenuation of the mass lying in the detector's corresponding ray path.

The output signals generated by the X-ray detectors are normally processed by a signal processing portion (not shown) of the CT system. The signal processing portion generally includes a data acquisition system (DAS) which filters the output signals generated by the X-ray detectors to improve their signal-to-noise ratio (SNR). The output signals generated by the DAS during a measuring interval are commonly referred to as a "projection" or "view" and the angular orientation of the disk 16, source 12 and detector system 14 corresponding to a particular projection is referred to as the "projection angle."

FIG. 2 illustrates the orientation of the disk 16, X-ray source 12 and detector system 14 for generation of a fan beam data point $P_f(\beta, \gamma)$ at a projection angle $\beta$ and a detector angle $\gamma$. A center line 40, which is used to define reference orientations, extends from the focal spot of the X-ray source 12 through the z-axis at the mechanical center of rotation 18. The projection angle $\beta$ is defined as the angle between a vertical axis and the center line 40. Each individual detector in system 14 has an associated detector angle $\gamma$ that is also defined with respect to the center line 40. By definition, the center line 40 intersects the detector system 14 at a reference detector angle $\gamma$ of 0°.

A symmetric detector system 14 as shown in FIG. 2 extends from a detector angle of $-\delta$ to $+\delta$, where $\delta$ is one-half the fan angle. A fan beam view or projection $P_f(\beta,\gamma)$ generated by symmetric detector system 14 includes a set of data points $P_f(\beta,\gamma)$, generated by all the detectors at the detector angles from $-\delta$ to $+\delta$ for the projection angle $\beta$. Asymmetric detector systems are also well known.

During a scan, the disk 16 rotates smoothly and continuously around the object being scanned, allowing the scanner 10 to generate a set of projections $P_f(\beta,\gamma)$ at the corresponding set of projection angles $\beta$. In a conventional scan, the patient remains at the constant z-axis position during the scan. When obtaining multiple scans, the patient is stepped along the z-axis between scans. These processes are commonly referred to as "step-and-shoot" scanning or "constant-z-axis" (CZA) scanning. Using well-known algorithms, such as the inverse Radon transform, a tomogram may be generated from a set of projections that all share the same scanning plane normal to the z-axis. This common scanning plane is typically referred to as the "slice plane."

A tomogram is a representation of the density of a two-dimensional slice along the slice plane of the object being scanned. The process of generating a tomogram from the projections is commonly referred to as "reconstruction," since the tomogram may be thought of as being reconstructed from the projection data. The reconstruction process can include several steps including convolution to deblur the data, rebinning to form parallel-ray data from the fan-beam-ray data and back projection in which image data for each image pixel is generated from the projection data. In CZA scanning, for a particular image slice, all the projections share a common scanning plane, so these projections may be applied directly to the back projector for generation of a tomogram.

The step-and-shoot CZA scanning approach can be a slow process. During this time consuming approach, the patient can be exposed to high amounts of X-ray radiation. Also, as the scanning table is moved between each scan, patient motion can result, causing motion and misregistration artifacts which result in reduced image quality.

Several approaches have been developed to decrease the time required to obtain a full scan of an object. One of these approaches is helical or spiral scanning in which the object being scanned is translated along the z-axis while the disk 16 with source 12 and linear detector array 14 are rotated about the patient. In helical scanning, the projections $P_f(\beta,\gamma)$ are normally acquired such that z is linearly related to the view angle $\beta$ so that $z(\beta)=c\beta$, where c is a constant. This form of helical scanning is commonly referred to as constant-speed-helical (CSH) scanning.

FIG. 3A illustrates the data collected during a conventional CZA scan, and FIG. 3B illustrates the data collected during a CSH scan. As shown in FIG. 3A, if the X-ray source 12 and the detector system 14 are rotated about the object 20 while the object remains at a fixed z-axis location, the scanning planes associated with all the projections collected by the detector system 14 will all lie in a common slice plane 50. As shown in FIG. 3B, if the object 20 is continuously translated in the direction of the z-axis while the disk is rotated about the object 20, none of the scanning planes will be co-planar. Rather, the scanning plane associated with each projection will lie at a unique position along the z-axis at a locus point on a helical set of loci. FIG. 3B illustrates the z-axis coordinate of the scanning planes corresponding to helical projection angles in the interval (0, 10π). Since the value of each projection depends on the z-axis location of the patient, each projection may be considered a function of two variables $\beta$ and z.

In CZA scanning, all the projections share a common scanning plane, so these projections may be applied directly to the back projector to generate a tomogram. In CSH scanning however, each projection has a unique scanning plane located at a unique z-axis coordinate, so CSH projections may not be applied directly to a back projector. However, the data collected during a CSH scan can be interpolated in various fashions to generate a set of interpolated projections that do all share a common scanning plane extending normal to the z-axis. Each interpolated projection, for example, may be generated by combining two projections taken at equivalent projection angles and at different z-axis positions. These interpolated projections may be treated as CZA data and applied to a back projector to generate a tomogram.

CSH scanning requires some form of interpolation to generate a tomogram, and tomograms generated by CSH scanning therefore tend to be characterized by image artifacts. Also, since the CSH scan projection data, which are collected over an interval of z-axis locations, are combined to generate the interpolated CZA scan data, tomograms generated during CSH scanning have a wider effective slice plane width and, therefore, lower z-axis resolution, than tomograms generated by CZA scanning. However, helical scanning advantageously permits rapid scanning of a large volume of a patient. For example, in a time interval short enough to permit a patient comfortably to hold his or her breath (and thereby remain relatively motionless), a helical scan can collect enough data to fully scan an entire organ such as a kidney.

Another approach to decreasing scan time over CZA scanning is commonly referred to as "cone-beam scanning," in which a three-dimensional volume of the object or patient is scanned at once. In cone-beam scanning, the detection system includes a two-dimensional array of detectors instead of the one-dimensional array used in conventional scanning. The X-ray output from the source diverges in two dimensions to produce the equivalent of multiple fan beams along the z-axis dimension which illuminate multiple rows of plural detectors and therefore form a two-dimensional projection on the array.

In one form of a cone-beam system, the patient or object is maintained in a stationary z-axis position while the source and two-dimensional detector array are rotated around the patient or object. The patient is then moved to a new z-axis position, and the scan is repeated. In this type of step-and-shoot or "stationary cone beam" system, rather than sweeping out a plane, a volume of the object is scanned. After one volume is scanned, the source and detector are stepped along the z-axis to scan the next volume. Still another approach used to decrease scan time is helical cone-beam (HCB) scanning, in which a cone-beam configuration, i.e., a source and two-dimensional detector array, are rotated around the patient while the patient is continuously translated in the z-direction.

Standard two-dimensional reconstruction techniques, such as 2D filtered back projection (FBP), are used to reconstruct CZA and interpolated CSH data in non-cone-beam systems. FBP requires that the set of projections used for reconstruction lie in the same plane. This condition is satisfied in CZA scanning, and interpolation is used in CSH scanning to produce a set of interpolated or simulated linear projections which effectively meet this requirement. In either case, 2D FBP is an efficient means of producing image data from the 1D fan-beam projection data.

In cone-beam geometry, the required condition is only satisfied for a detector row coplanar with the source in a plane perpendicular to the z-axis, i.e., the center detector row. In stationary cone-beam CT, a 1D projection defined by the source and a given detector row will intersect a different slice in the object as the gantry rotates. Conventional 2D FBP can be used to reconstruct cone-beam data by treating each row as an independent 1D projection. This approximation ignores the cone-beam geometry and results in image artifacts such as streaks and lowering of the reconstructed density. A better approximate method used to reconstruct cone-beam data is known as the Feldkamp algorithm and is described in L. A. Feldkamp, et al., "Practical cone-beam algorithm," *J. Opt. Soc. Am.* 1, pp. 612–619, (1984).

In the Feldkamp algorithm, the rays are back projected in the three-dimensional cone. Algorithms such as Feldkamp, which attempt to incorporate the true cone-beam geometry of the data, are referred to as three-dimensional filtered back projection (3D-FBP) algorithms. Three-dimensional algorithms reconstructing HCB data have also been developed. Examples of these algorithms are described in the following papers.

1. H. Kudo and T. Saito, "Three-dimensional helical-scan computed tomography using cone-beam projections," *Journal of Electronics, Information, and Communication Society*, J74-D-II, 1108–1114, (1991).
2. D. X. Yan and R. Leahy, "Cone-beam tomography with circular, elliptical and spiral orbits," *Phys. Med. Biol.* 37, 493–506, (1992).
3. S. Schaller, T. Flohr and P. Steffen, "New efficient Fourier reconstruction method for approximate image reconstruction in spiral cone-beam, CT at small cone angles," *SPIE International Symposium on Medical Imaging*, February, 1997.
4. G. Wang, T-H Lin, P. Cheng and D. M. Shinozaki, "a general cone beam algorithm," *IEEE Trans. Med. Imag.* 12, 486–496, (1993).

A disadvantage of 3D reconstruction algorithms is that they cannot be used with common 2D reconstruction hardware, and, consequently, custom 3D back projection hardware must be built to accommodate them.

In many CT scanning applications, it is desirable to pre-screen a region before performing reconstruction. For example, certain suspect objects, such as tumors, may be identified by a pre-screening process for further closer examination during medical CT imaging. Also, CT scanning is applicable to identification of contraband items, such as weapons and explosives in baggage being carried or loaded onto commercial aircraft. It is often desirable to pre-screen baggage to identify suspect bags which can then be subject to full CT image reconstruction if the pre-screening process identifies a suspect target. In one prior art approach to pre-screening, a separate line scanner is used to generate a two-dimensional projection through the object being scanned, e.g., patient baggage, to identify suspect areas. Where a suspect target is identified, the object can then be subjected to full CT scanning and reconstruction. This process can be time consuming and, in the baggage scanning application, can be impractical, considering the rate at which bags must be screened at a commercial airport.

OBJECTS OF THE INVENTION

It is an object of the present invention to substantially overcome the above-identified drawbacks of the prior art.

Another object of the invention is to provide a CT system with reduced image artifacts.

Yet another object of the invention is to provide a CT system which provides the image quality of a three-dimensional reconstruction algorithm using two-dimensional reconstruction hardware.

Still another object of the invention is to realize the foregoing objects in a helical cone-beam scanning CT system.

It is a further object of the invention to provide an efficient means of producing a two-dimensional projection image of an object from CT scan data which can be applied to situations such as baggage scanning in which high scanning throughout is required.

It is a further object of the invention to provide target detection such as by summing masses associated with CT image volume elements where the volume elements are tilted with respect to the longitudinal axis of the scanning region of a CT scanning system.

SUMMARY OF THE INVENTION

Accordingly, the present invention is directed to a CT apparatus and method for generating image data for a region. The region defines a longitudinal axis and an orthogonal transverse axis. A radiation source and an array of detectors are used to scan the region to generate scanned data that is representative of the region. In one embodiment, a helical cone-beam scanning approach is used to scan the region. At each of a plurality of positions along the longitudinal axis, or, equivalently, at each of a plurality of projection angles, a two-dimensional image data slice is defined. Each data slice defines a slice plane which is tilted with respect to the longitudinal axis of the region. That is, the normal axis of each slice plane is tilted at a tilt angle with respect to the longitudinal axis of the region. The normal axis also defines a rotation angle with the transverse axis of the region. Successive slices along the longitudinal axis define normal axes that define equal tilt angles with the longitudinal axis of the region. Also, the rotation angle for successive slices increases along the longitudinal axis. The result of the constant tilt angle and increase in rotation angle is that the normal axes describe a precession and nutation about the longitudinal axis of the region through successive slices. In this geometry, the slices can be said to be nutated with respect to each other. At each of the image slices, image data is computed from the scan data to produce the image of the region. The reconstruction process for successive slices is hereinafter referred to as the "nutating slice reconstruction" (NSR) approach.

The NSR approach of the invention is preferably used to reconstruct helical cone-beam data using conventional two-dimensional filtered back projection. In NSR, a set of 1D fan-beam projections is extracted from the 2D cone-beam projection data set using interpolation. NSR therefore involves the selection of 2D fan-beam data from 3D cone-beam data. The 1D projection set corresponds to reconstructing a tilted slice whose geometry is chosen to minimize the adverse effects of the cone angle on image quality when using 2D FBP.

Traditionally, when reconstructing a series of slices, each slice is the x-y plane at a different location along the z-axis. That is, all the slices in the series are parallel to each other. In NSR, the normal vector to the reconstructed slice plane is tilted by a small angle with respect to the z-axis. In a series of adjacent slices reconstructed with NSR, the normal vector to the slice plane precesses about the z-axis and the slices are not parallel to each other. The term "nutated" in NSR refers to the relative orientation of adjacent slices. If parallel slices are required, the resultant NSR image data can be interpolated to provide parallel slices.

In one embodiment, the x-ray source is a cone-beam source, and the array of detectors is a two-dimensional array. The scan data for each projection is determined from a predefined one-dimensional line of detectors on the array. The detectors used for a given projection or slice are associated with the projection angle or position along the longitudinal axis. At each position or projection angle, a group of detectors is chosen which minimizes the error in the measurement. Each slice is therefore associated with a projection angle, a longitudinal position and a group of detectors which in general defines a one-dimensional "fan-beam" projection on the two-dimensional detector array.

When a particular slice is reconstructed, its scan data is generated from its associated detectors in the two-dimensional array.

In another aspect, the invention is directed to an apparatus and method for providing a two-dimensional projection image of a region from the scan data generated for the region. Each nutated slice is generated from a set of fan beam views or projections which are rebinned to parallel-ray projection data, with each view or projection being obtained at a respective view angle. In the present invention, a projection angle for the two-dimensional projection image is selected as the angle at which the two-dimensional projection image is to be taken. For each slice, the view angle associated with the selected projection angle is identified, and the parallel-ray projection data associated with that view angle is selected. The two-dimensional projection image at the selected projection angle is generated by combining the selected parallel-ray projection data for the selected view angle for each slice in the scan data. In one embodiment, multiple two-dimensional projection images can be generated at multiple projection angles. These multiple projection images can be generated from a single set of scan data. The length of the projection image along the z-axis is equal to the axial extent of the slices used to form the projection image.

In one embodiment, the two-dimensional projection image can be used to determine the size of an object projected at the selected projection angle. By identifying object boundaries in the two-dimensional projection image, the size of the object and its location within the field of view can be determined. The object size and location can also then be used to identify the object and to identify regions of the field of view that need not be reconstructed since they provide no information regarding the object. This "adaptive field of view" can be very useful in systems in which scanning throughput is important, such as in a baggage scanning system. This feature is described and claimed in a U.S. patent application entitled "Computed Tomography Scanning Apparatus and Method Using Adaptive Reconstruction Window," by Bernard M. Gordon, et al. U.S. Ser. No. 08/949,127, filed on even date herewith, of common assignee and incorporated herein by reference.

In another aspect, the invention is directed to a method and apparatus for detecting targets such as explosives using the nutated image slices generated in accordance with the nutating slice reconstruction approach of the invention. In this aspect of the invention, tilt or nutation of the slices is compensated for to provide accurate target identifications. Scan data for a region in which an object is located are obtained by scanning the region with a radiation source and an array of detectors. Using the scan data, a plurality of non-parallel image data slices are defined to correspond with a plurality of positions along the longitudinal axis of the region. Each slice defines a plurality of image volume elements or "voxels" which are tilted with respect to the longitudinal axis of the region, and each voxel is associated with an image density value derived from the scan data. A correction factor is applied to the image density values of the tilted volume elements to compensate for the tilt of the image volume elements.

In one embodiment, the image density values are used to determine the mass of an object under analysis such as an explosive. The determination of mass of an explosive is helpful to assess the potential threat it poses. The density value for each voxel that is related to the object can be multiplied by its volume to determine the mass represented by the voxel. The computed masses of all the voxels identified as being related to the target, i.e., explosive, are then summed to determine the total mass of the object. Compensating for the tilt of the voxel provides a more accurate determination of mass such that a better assessment of threat is obtained.

As described above, a total object mass can be computed by identifying the voxels which are associated with the object of interest, i.e., explosive, compensating for tilt of the voxels and totaling the masses for the identified voxels. Identifying related voxels can be accomplished applying the density value associated with each voxel to a density value threshold. The threshold is selected based on known densities of known materials, i.e., explosives. Those values which exceed the threshold are concluded to be associated with the target material, and, therefore, their associated voxels are concluded to be related to an image of the target material. These voxels are used in the total mass computation. In the present invention, they are applied to a correction factor used to compensate of the tilt of the voxels with respect to the longitudinal axis of the region. The products of the compensated volumes and related densities are then summed to determine the total mass.

The density thresholding can be accomplished by applying the volume elements to a multiplying window function. Values which exceed the threshold are applied to a unit multiplier of the window and those that do not exceed the threshold are applied to a zero multiplier to effectively discard them from the total mass computation.

In another aspect, the present invention is directed to a processing method and system which provide for efficient processing of the nutated image data slices generated in accordance with the nutating slice reconstruction approach of the invention. This aspect of the invention provides a processing architecture which provides multiple independent processing paths for groups of image slice data instead of a more conventional pipeline processing approach in which the slices would be processed serially. In accordance with this aspect of the invention, scan data for a region are generated by scanning the region with a radiation source and an array of detectors. To scan the region, at least the radiation source rotates about a longitudinal axis of the region through a plurality of view angles while the radiation source emits radiation toward the array of the detectors. The scan data therefore comprise a plurality of sets of projection data, each set of projection data being acquired at a respective view angle. In accordance with the nutating slice reconstruction approach of the invention, each set of projection data includes a plurality of projections, e.g., fan-beam projections. Each fan-beam projection in a set of projection data is used to generate an image data slice, a plurality of projections within each set of projection data being used to generate a respective plurality of image data slices. In addition, each image data slice is generated from a plurality of fan-beam projections, with a single fan-beam projection being taken from each of a plurality of sets of projection data for the slice. Therefore, in the present invention, slice data for each image data slice are generated from a respective associated set of fan-beam projections. Each image data slice is associated with a respective data storage element which, in one embodiment, is a memory circuit. Projections from the image data slice to be generated are stored in the data storage element. The stored projections from each data storage element are processed to generate slice data for the image data slice associated with the data storage element.

In one embodiment, a processor receives the scan data from the array of detectors and generates the fan-beam projections from the sets of projection data within the scan data in accordance with the NSR approach described above. The processor then transfers the projections to the data storage elements associated with the image data slices being generated. A demultiplexor circuit can be included between the processor and the data storage elements to control routing slice data projections to their associated data storage elements.

In one embodiment, instead of a single processor generating the projections in a pipeline fashion, a plurality of processors operating in parallel can be used. In this case, each image data slice to be generated is associated with a single processor which generates the projections for that slice. The projections are transferred by the associated processor to an associated data storage element, e.g., memory circuit, from which the projections will be retrieved to generate the slice data for the image data slice. In one embodiment, one or more demultiplexor circuits can be placed between the plurality of processors and a plurality of data storage elements to control transfer of the projections to the data storage elements. In one embodiment, all of the processors can transfer projections to any of the data storage elements. In another embodiment, each processor can only transfer projections to a selected group of data elements. By using multiple processors, processing the scan data into image data slices is accomplished much more quickly and efficiently than in the single processor pipeline approach.

In one embodiment, the slice data are further processed to generate actual image data slices which will in turn be used to generate an image of the region. This further processing can include filtering and/or backprojection to generate the image slices. As mentioned above, the projections generated by the processor and/or processors are typically fan-beam projections. In one embodiment, further processing can be performed on the fan-beam projections to rebin them to parallel-beam projections. In one embodiment, where multiple processors are used, one of the processors can be used to perform the rebinning procedure while the others continue to be used to generate projections. The one processor can be temporarily switched to the rebinning procedure and then switched back to generating projections after rebinning is complete. This saves considerable hardware by eliminating the need for an additional processor dedicated to rebinning.

The CT apparatus and method of the invention provide numerous advantages over prior approaches. It provides a three-dimensional scanning approach in the form of helical cone-beam scanning, which is far less time consuming than prior approaches using linear detector arrays. It provides a reconstruction process which results in image quality comparable to three-dimensional reconstruction algorithms, but does not require three-dimensional reconstruction hardware. The much simpler two-dimensional reconstruction hardware is used. Furthermore, the approach to generating two-dimensional projection images used in the invention is much more efficient than prior approaches such as those used in prior baggage scanning systems in which a separate line scanner is used to produce the projection image as part of a pre-scanning process. By compensating for nutation or tilt of voxels, the present invention can provide target detection and target size and mass determination with improved accuracy over an approach which does not compensate for voxel tilt. Also, by applying the nutating slice reconstruction approach to the parallel processing architecture of the invention, images can be generated much more efficiently than if a conventional pipeline processing approach were used.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE DRAWINGS

Figure 4:
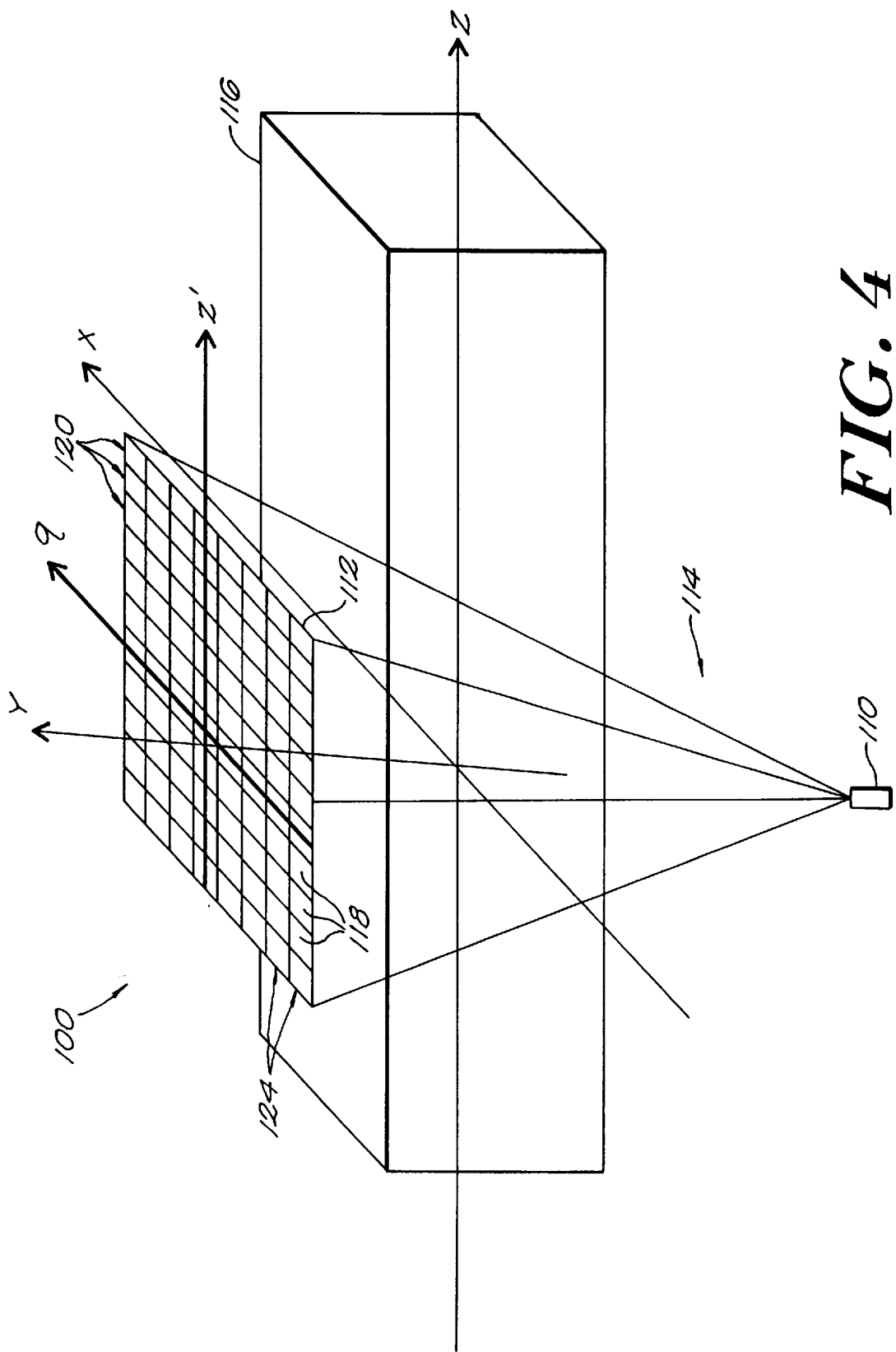
FIG. 4 is a simplified schematic diagram which illustrates the spatial relationships among the source, detectors and scanning object in a CT scanner in accordance with the present invention.

FIG. 4 is a schematic diagram which illustrates the functional operation of one embodiment of the CT scanning system 100 of the invention. The system includes an x-ray source 110 which emits x-rays toward a two-dimensional x-ray detector array 112. The detector array 112 is shown as a flat array having coordinates z' and q. A curved array can also be used. The x-rays diverge in a cone-beam which passes through an object 116 being scanned. The x-rays, attenuated by the object 116, are detected by the individual detectors 118 in the detector array 112. The array 112 of detectors includes multiple rows 120 of detectors along the z'-axis and multiple columns 124 along the q-axis. The cone-beam 114 therefore can be considered to consist of multiple fan beams spread along the q-axis and adjacent to each other along the z'-axis. The object 116 defines a z-axis (also referred to herein as the longitudinal axis) and an orthogonal x-axis (also referred to herein as the transverse axis).

As discussed above, the x-ray source 110 and detector array 112 are secured to diametrically opposite sides of an annular shaped disk (not shown). The disk is rotatably mounted within a gantry support (not shown) such that the source 110 and detector array 112 are simultaneously rotatable about the z-axis and, hence, about the object 116 being scanned.

In one embodiment, the system 100 uses helical cone-beam scanning such that, as the gantry rotates about the z-axis, the gantry and object 116 are also translated relative to one another along the z-axis. The gantry with source and detector array rotate through an increasing projection angle $\beta$ as the gantry translates along the z-axis. At each projection angle, scan data are collected by the detector array. Image data in the form of a series of image slices are then reconstructed from the projection data. Each slice defines a planar configuration of image data and is generated from a predefined collection of scan data gathered as the source and detector array rotate.

In the present invention, even though a three-dimensional scanning approach, namely, helical cone-beam scanning, is used, a two-dimensional reconstruction approach can be used to generate the image data. To accomplish this, the present invention projects a two-dimensional data slice onto the two-dimensional array of detectors such that the projection of the slice at each projection angle can be considered a one-dimensional fan-beam projection. In the general case, the projection onto the array falls on a group of detectors which are not necessary in a single row or column. In fact, in general, the projection will extend across several rows and columns. In the present invention these rows and columns are identified for each projection angle. A value is generated for each location at each projection angle from the projection data, in one embodiment, by interpolating the projection data. Thus, for each projection angle, a "fan beam" of detector data is generated, very much analogous to the fan beam data generated in two-dimensional fan beam scanning applications which use a linear detector array. The result is a set of "fan beam" data for each projection angle. In the present invention, once these data are generated, they can be applied to any suitable two-dimensional back projection algorithm to reconstruct image slices as if it were actual fan beam data.

In the present invention, at each projection angle the rows and columns of the detector array which receive the associated fan beam are identified before an actual scan is performed. In one embodiment, a simulation or calibration scan, which simulates helical cone-beam scanning of an opaque disk, can be performed. At each projection angle, the simulated projection of the disk onto the array is recorded in the detector data. After the disk is entirely scanned, the projection data is analyzed to determine which rows and columns of the array receive the projection of the disk at each projection angle. The simulation process creates a "z-interpolation table" in which each projection angle is associated with a group of detector rows and columns which should be read during subsequent scans of actual objects to generate the 1D fan beam data. When the desired slices are reconstructed, the fan beam data at each projection angle are detected from the associated array row and columns stored in the z-interpolation table. In another embodiment, an actual opaque disk can be subjected to helical cone-beam scanning with an actual source and detector array to generate the z-interpolation table.

Many fan-beam projections are collected for each slice to be reconstructed. For example, in one embodiment, data is collected for one half of a complete revolution of the gantry (180°) plus the angle subtended by the detector array. In one embodiment, the array subtends a 60° angle; hence, each slice is generated from data collected during 240° of gantry revolution. In one embodiment, projections are produced every 1° of projection angle. Therefore, in this embodiment, each slice is generated from 240 fan-beam projections. The groups of projections for successive slices along the z-axis can overlap each other. For example, slices may be generated every 12° of rotation. Therefore, in the embodiment described above, 228 out of 240 projections are shared by each pair of adjacent slices.

As mentioned above, in general, the reconstructed slices in the present invention are not perpendicular to the z-axis as in conventional non-cone-beam scanning. Instead, they are tilted or nutated with respect to the z-axis, and the normal axes of successive slices precess about the z-axis. Each slice defines a slice plane having a normal axis which forms an angle with the longitudinal or z-axis about which the scanning system rotates. The use of a tilted slice reduces the error in the reconstructed slice data. The angle of tilt can be determined using the simulation scan mentioned above and also described below in more detail. The selected angle is the angle at which the projection of the opaque disk onto the array produces the least image reconstruction error.

Figure 5:
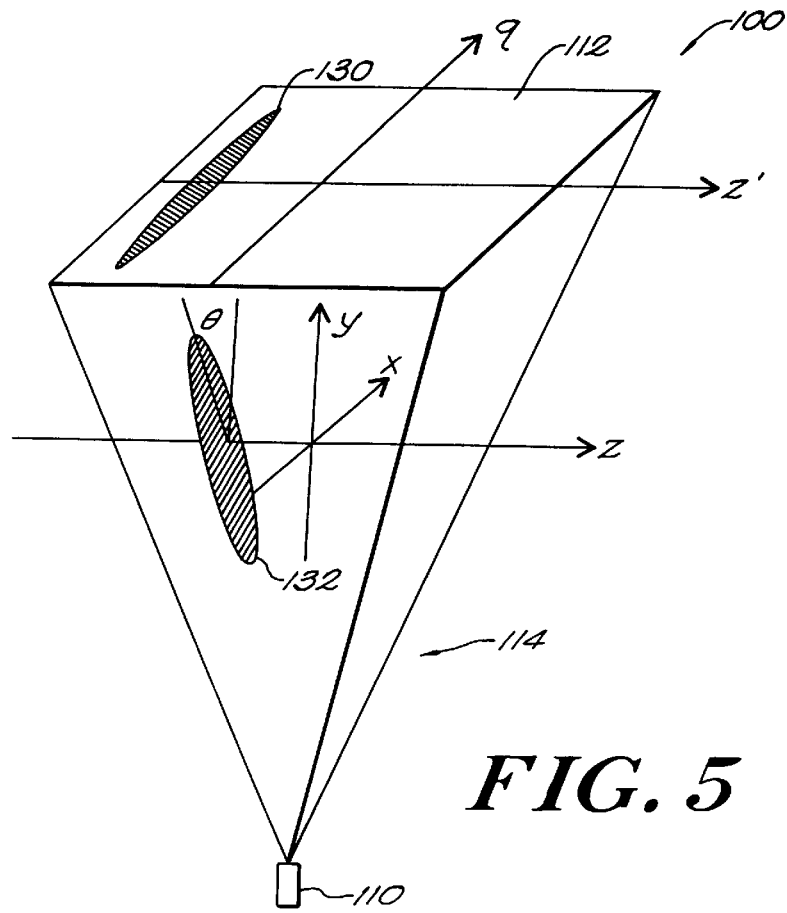
FIG. 5 is a simplified schematic illustration of the projection of a tilted slice onto a two-dimensional detector array.

FIG. 5 is a schematic diagram which illustrates acquisition of data during the simulation scan for a single projection at a single angle using a tilted reconstruction image slice represented by the titled opaque disk 132. The cone beam of x-rays 114 is emitted by the source 110 and passes through the object (not shown) and illuminates the flat two-dimensional detector array 112. As shown, the plane of the slice or disk 132 forms an angle $\theta$ with an axis orthogonal to the z-axis. Equivalently, the normal axis to the slice plane forms the angle $\theta$ with the z-axis.

An elliptical projection or shadow 130 of the tilted disk 132 is projected onto the detector array 112. As the source 110 and detector array 112 rotate about and move along the z-axis, the location and shape of the projection 130 of the disk 132 changes. As the disk 132 moves through the scanning volume, or, equivalently, as the source and detector are scanned past the slice, the area of the projected ellipse changes. The tilt angle $\theta$ is fixed as the disk 132 translates through the detector array.

The spread of the ellipse (the length of its minor axis) at each projection angle is an indication of the error introduced in reconstructing the slice at that projection angle. The object is to select a disk geometry that minimizes the total projected ellipse area over all of the projection angles, e.g., 240°, for the tilted slice being reconstructed. The area is minimized by reconstructing a tilted slice where the normal to the slice plane is tilted by a small angle $\theta$.

Figure 6:
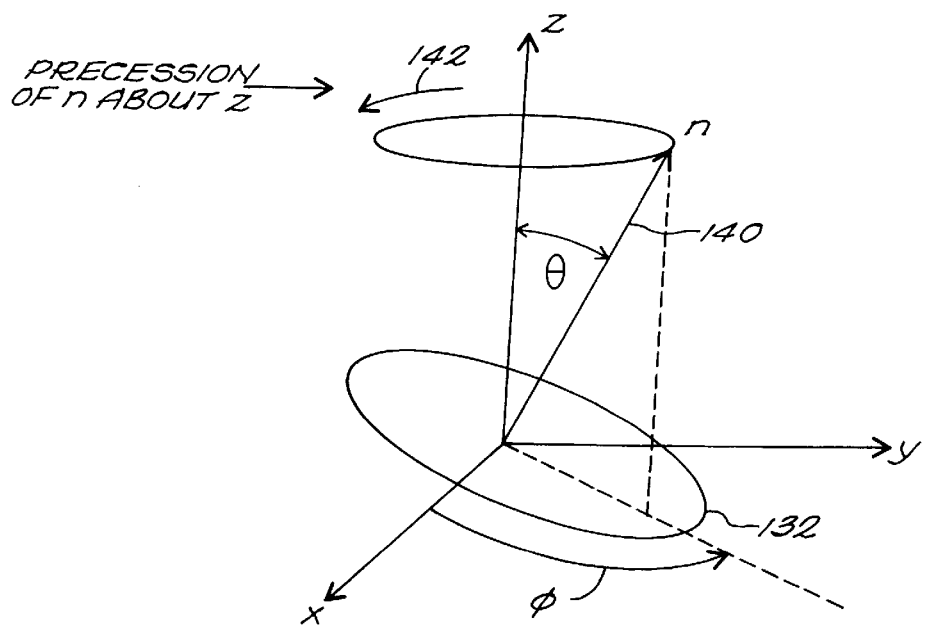
FIG. 6 is a simplified schematic illustration of the tilt and rotation angle of a tilted slice in accordance with the present invention.

FIG. 6 is a schematic diagram which illustrates the relationship between a tilted slice 132 and the system axes. As mentioned above, the normal 140 to the slice plane forms an angle θ with the z-axis, which is referred to herein as the tilt angle or nutation angle. The normal axis 140 also forms a rotation angle φ with the x-axis or transverse axis of the system.

As described above, each slice can be reconstructed from projections whose projection angles span the range of 0° to 180° plus the array angle (60°). At one degree per projection, each slice is reconstructed from 240 projections. For any given slice, a particular slice tilt angle θ and rotation angle φ will yield the smallest error over all 240 projections. In one embodiment, adjacent slices are reconstructed every twelve degrees of rotation from overlapping sets of 240 projections shifted by twelve degrees. Each slice is associated with a tilt angle θ and rotation angle φ which minimize the reconstruction error in the slice. In one embodiment, for successive slices, the tilt angle θ remains constant and the rotation angle φ increases or decreases to define a rotation or precession of the normal axes of slices about the z-axis, as illustrated by the arrow 142 in FIG. 6. The error at each tilt angle is determined by summing the total area of all disk projections over the entire 240° of data. The tilt angle yielding the minimum total error is taken as the tilt angle. In one embodiment, a tilt angle of approximately 1.45° is used.

Figure 7:
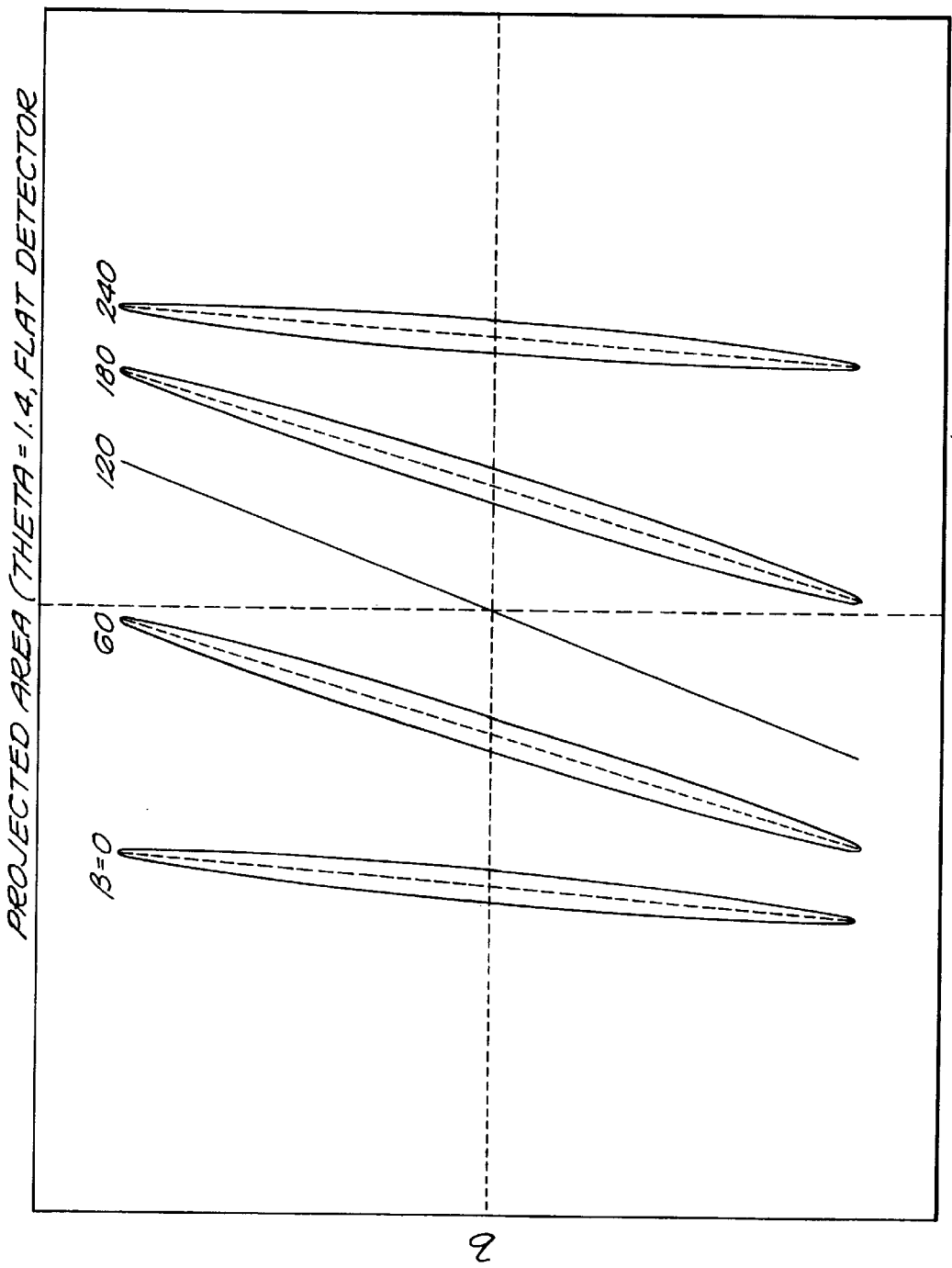
FIG. 7 is a simplified schematic diagram of projections of a tilted slice onto a flat detector array.

FIG. 7 is a schematic diagram showing projections of the disk 132 at a tilt angle of 1.4° passing through the scan region. The curves show projections at projection angles, or view angles, of β=0°, 60°, 120°, 180°, and 240°. The figure assumes a flat detector array.

Figure 8:
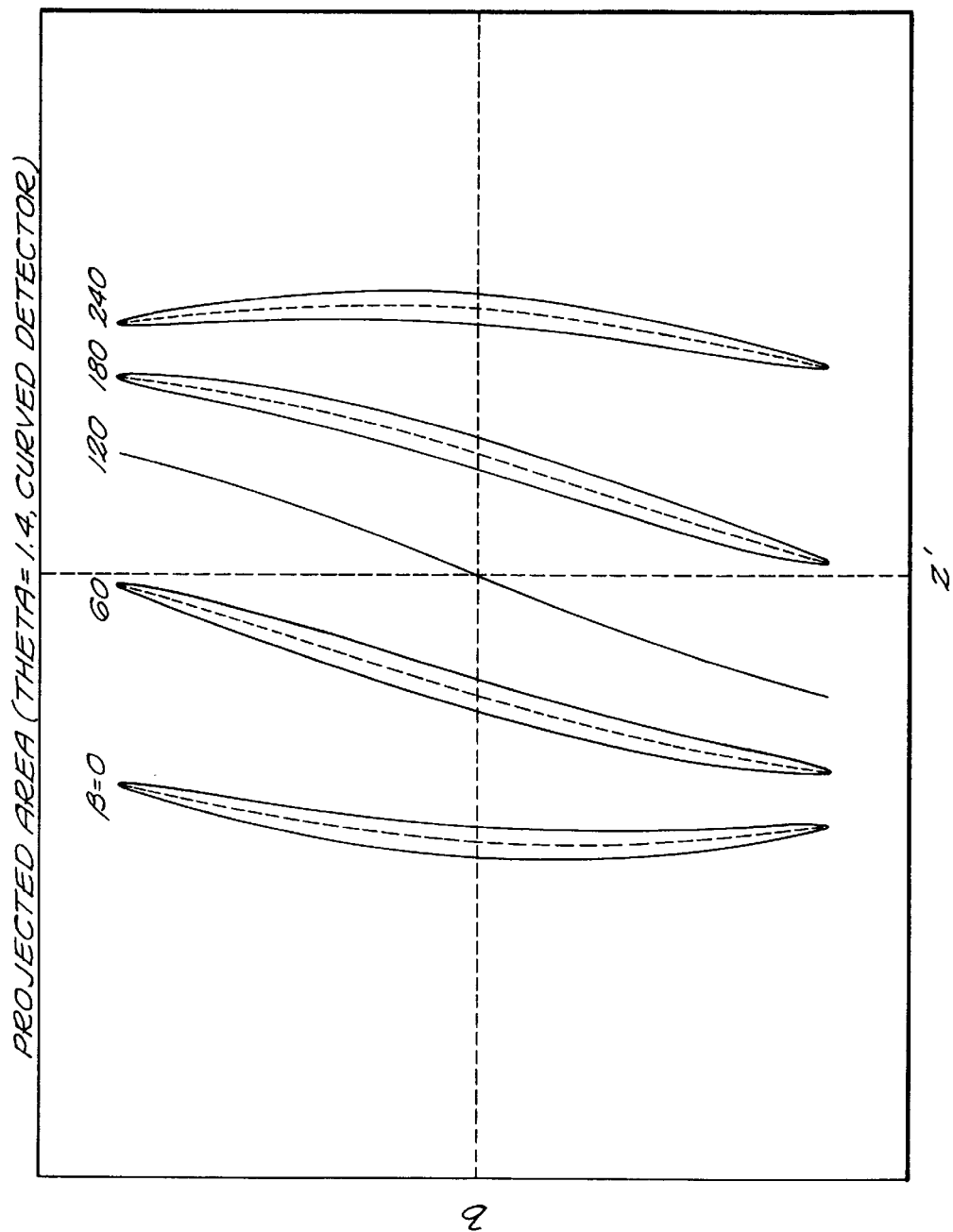
FIG. 8 is a simplified schematic diagram of projections of a tilted slice onto a curved detector array.

As noted above, the detector array can also be curved. In that case, the projections of the disk or slice onto the array will not be ellipses as shown in FIG. 7. They will actually be curved figures as shown in FIG. 8. FIG. 8 shows the same projections as FIG. 7 with a tilt angle of 1.4°, except that the detector array 112 is curved.

Figure 9:
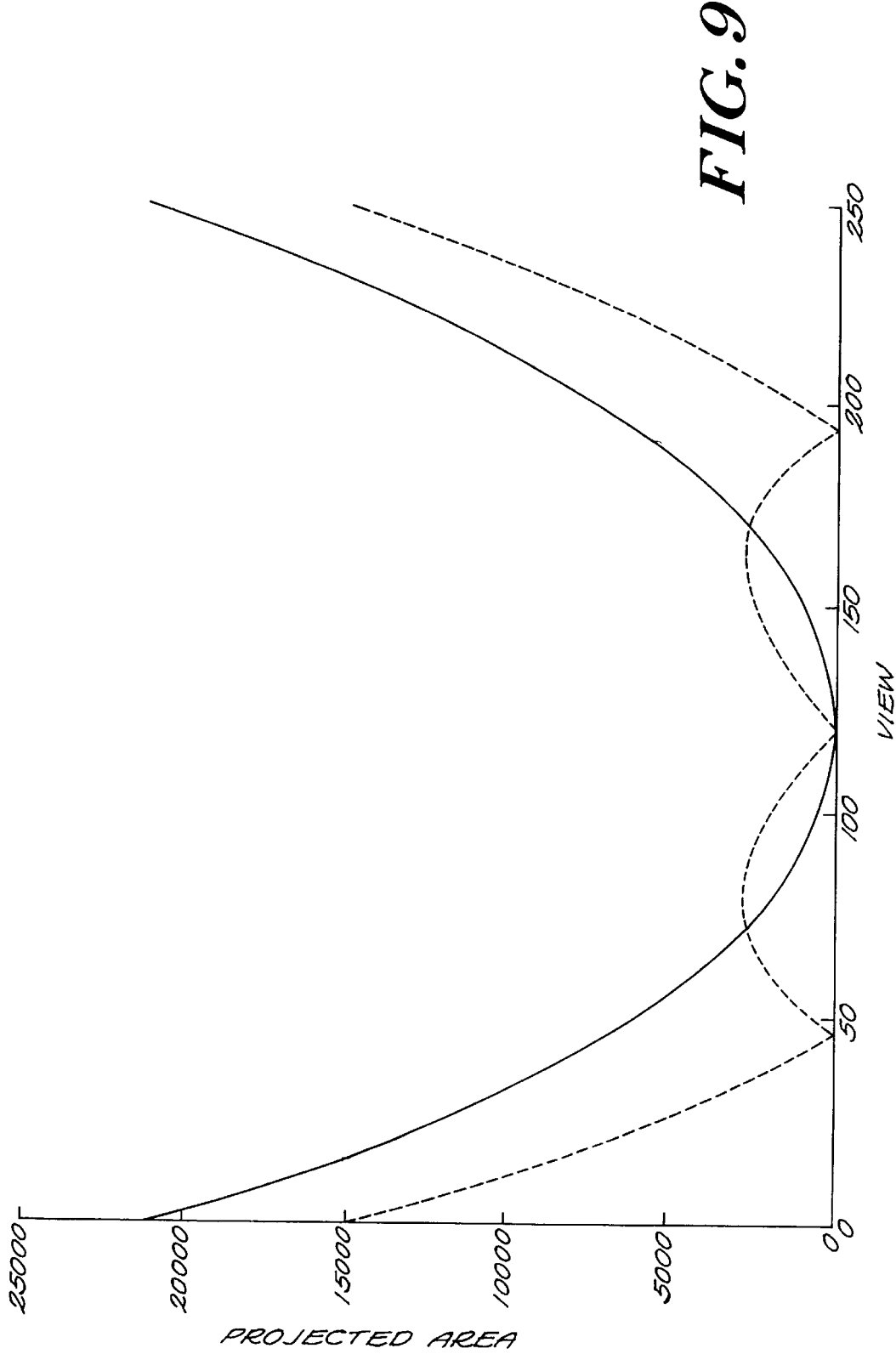
FIG. 9 contain schematic plots of the total projected area of a tilted slice and a perpendicular slice versus view angle.

An example of the total projection area plotted as a function of view is shown in FIG. 9. The dashed line shows the area for a tilt angle of 1.45° and the solid curve shows the area for no tilt angle. The tilt angle is chosen as the angle which minimizes the total area, which in one embodiment is determined to be 1.45°

Figure 10:
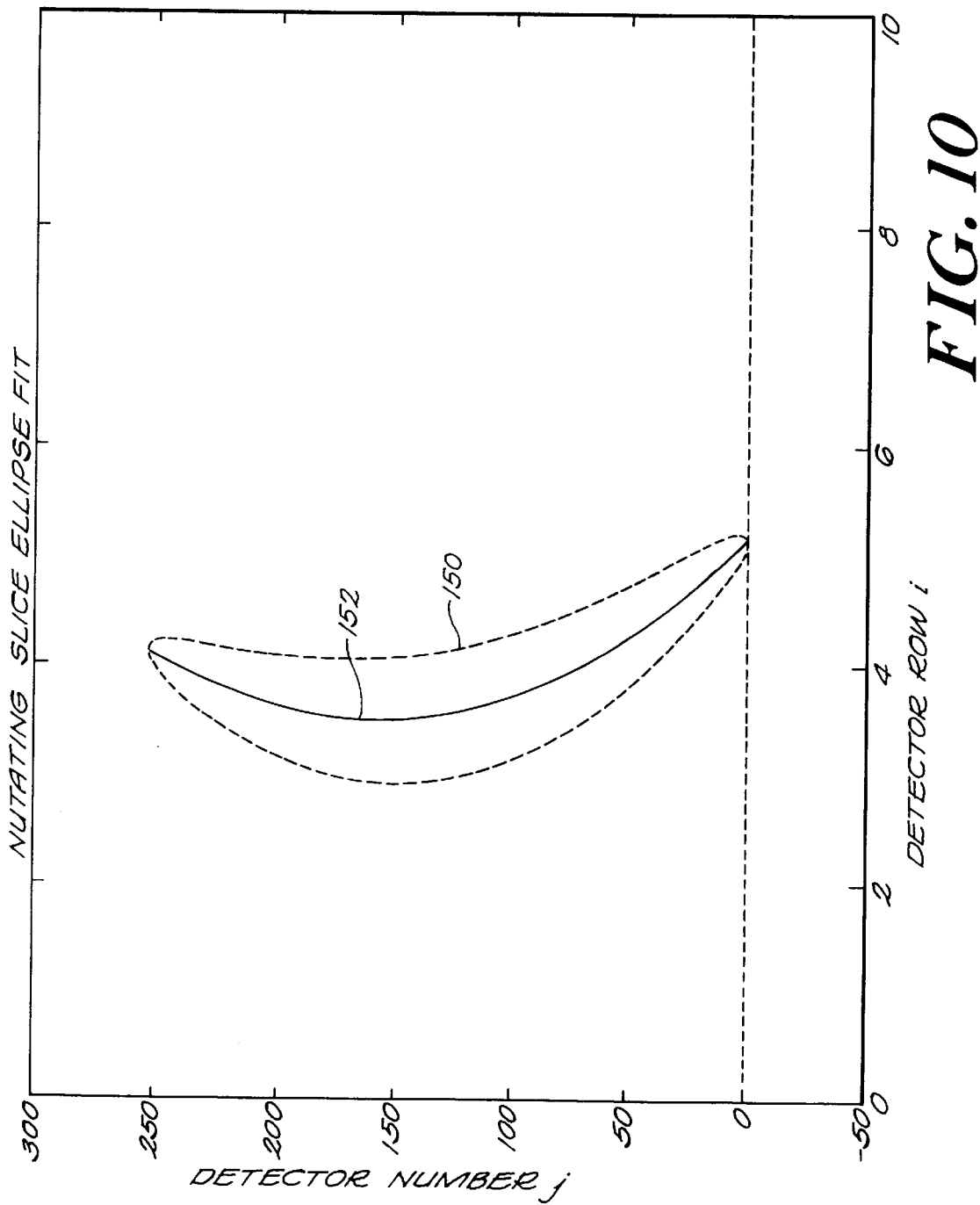
FIG. 10 is a simplified schematic diagram of a slice projection onto a curved detector array.

As described above, the simulation scan can also be used to identify the pixel rows and columns used for each projection at each different projection angle. FIG. 10 is an example of a single tilted slice projection onto the curved detector array. All of the detectors on the array are read to identify the location of the projection 150 and, therefore, the detector rows and columns which should be read during future scans of actual objects at the particular projection angle. In this embodiment, the array includes ten rows i of 252 detectors j each. The dashed line 150 indicates the spread of the curved elliptical projection on the array. The solid line 152 identifies the line of detectors that are read during subsequent scans at this particular projection angle. The line 152 is identified by computing the centroid of the detector values across each row. It is this solid line 152 that defines the detectors to be read during subsequent scans of an actual object. This process is completed at each projection angle for the slice to be reconstructed. The simulation or calibration process associates each projection angle with a row and column value and stores them together in a "z-interpolation table." This table is read during subsequent scans to identify the scan data used to reconstruct actual slices.

Figure 11:
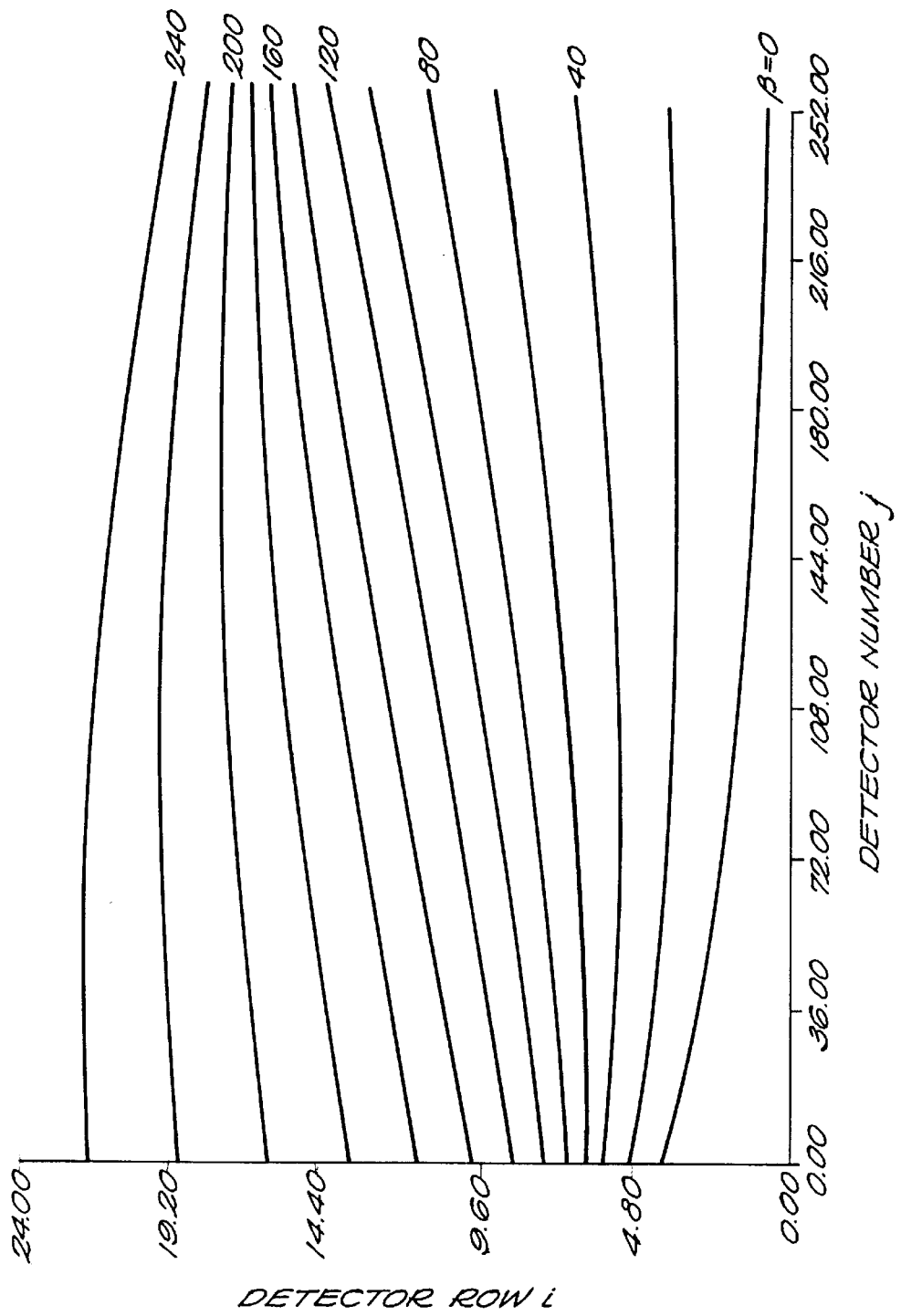
FIG. 11 is a simplified diagram showing slice projection lines on a two-dimensional curved array for projection angles between 0° and 240°, in increments of 20°.

FIG. 11 shows a set of disk projections on a two-dimensional curved array for a slice tilted at 1.45° at view angles between 0 and 240°, spaced by 20° each. These are the array row/column lines generated for each projection angle during the calibration scan. The row/column numbers plotted for each projection angle are stored in the z-interpolation table. The array used for this plot is a standard array consisting of 24 detector rows i of 252 detectors j each. As described above, each of the curved lines is identified by computing the centroid of the projection on the array at each view angle.

After the simulation scan is performed as described above to generate the z-interpolation table, actual scans of objects can be performed according to the following procedure. First, the projection data can be obtained by helical cone-beam scanning. Next, the projection data can be corrected for offsets, gain error and non-linear effects. Next, the HCB data is applied to the z-interpolation process, which extracts the desired fan-beam data. At each projection angle, detector row and column numbers are retrieved from the z-interpolation table, and X-ray intensity values at the identified detector rows and columns are recorded as the fan-beam data. In one embodiment, the z-interpolation process can proceed as follows: At each view, the process steps through each detector j, one at a time. For each detector, a row number I is identified from the z-interpolation table, which is in general some real number. Where the row number i is not a whole number, interpolation can be performed on the actual data values at the appropriate row numbers to identify a value for the particular detector as described below. In one embodiment, linear interpolation is used, but other forms of interpolation can be used.

For the remainder of the reconstruction process, the interpolated data values can be treated as if they were fan beam values obtained during a conventional two-dimensional scanning procedure. They can optionally be applied to a rebinning process to produce parallel-ray data. The rebinned two-dimensional data can then be applied to a conventional one-dimensional convolution procedure. Finally, the parallel-convolved data can be applied to a conventional two-dimensional back projection algorithm. The above process is repeated for each slice in the region.

A detailed mathematical description of the approach of the invention follows.

Let a continuous cone beam data set be given by $C(\beta,z',q)$, where β is the gantry rotation angle (or view angle), and q and z' are the position on the detector as shown in FIG. 4. To reconstruct one slice, the angular range of β must be at least 180° plus the fan angle. A reconstruction using the minimum number of projections is referred to as a halfscan. Let $\beta_h$ be the range of projection angles used for halfscan reconstruction. More views can be used if an overscan correction is desired. The method of overscan is discussed in detail below.

The method of NSR can be summarized as follows:

1. For a given β, where $0 \leq \beta < \beta_h$, extract a fan-beam projection, $F(\beta,q)$, from the cone beam data $C(\beta,z',q)$. The fan beam data are given by $$F(\beta,q) = C(\beta, L(\beta,q), q) \qquad (1),$$

where $L(\beta,q)$ is the line of the desired 1D projection $(z'=L(\beta,q))$. $F(\beta,q)$ may optionally be rebinned to parallel data at this stage. The rebinning is the preferred method due to the computational efficiency of back-projecting parallel views rather than fan views. The rebinning procedure is discussed in detail below.

2. Convolve $F(\beta,q)$ with an appropriate convolution kernel.

3. Backproject the convolved data using 2D-FBP.

The method of determining $L(\beta,q)$ and the optimization of the tilt angle are discussed below.

In reality, the cone beam data does not exist in continuous form and a method for discrete implementation is used. Specifically, the data on the line $L(\beta,q)$ must be determined by interpolating from discrete detectors. Let the cone beam data be given by $C[v,r,d]$, where $v$ is the view number (in the $\beta$ direction), $r$ is the detector row number (in the z-direction), and d is the detector channel number (in the q-direction) in a given row. Also let the limits be defined as $0 \leq v < N_h$, $0 \leq r < N_r$, and $0 \leq d < N_d$, where $N_h$ is the number of half scan views, $N_r$ is the number of rows, and $N_d$ is the number of detectors per row. The relations between the discrete and continuous variables are $$\beta = v \Delta_\beta \quad (2)$$

$$z' = (r - r_c) \omega_r \quad (3)$$

$$q = (d - d_c) \omega_d \quad (4)$$

where $\Delta_\beta$ is the angle between views, $\omega_r$ is the distance between rows, $\omega_d$ is the distance between detectors in a given row, $r_c$ is the row location of $z'=0$ and $d_c$ is the detector channel location of $q=0$.

$$r_c = \frac{N_r - 1}{2} \quad (5)$$

$$d_c = \frac{N_d - 1}{2} \quad (6)$$

As in the continuous case, the desired data lies along a line which intersects the ellipse. Let $F[v,d]$ be the fan beam data selected from $C[v,r,d]$. The interpolation in the r direction is referred to as the z-interpolation. Let $r'[v,d]$ be a lookup table which gives the location of the desired point in r for a given v and d. The fan data can be obtained by using linear interpolation in r. Namely, $$F[v,d] = (1-p)C[v,r_0,d] + pC[v,r_0+1,d] \quad (7)$$

where $r_0$ is the largest integer value less than or equal to $r'$, and $p = r' - r_0$.

The z-interpolation table can be determined by simulating projection data for the simulated tilted disk, as described above. The simulated disk has thickness equal to the detector row width projected to the isocenter. The attenuation coefficient is constant throughout the disk, and the photon energy is monoenergetic. In this way, a given projection ray measured through the disk is directly proportional to the thickness traversed. The center of the disk is located at the isocenter and oriented with a fixed tilt angle $\theta$. The disk travels in the z-direction at the specified table speed of the scanner. The location of the disk's center at the beginning and the end of data collection (i.e., at $v=0$ and $v=N_h-1$) is symmetric about $z=0$. The radius of the disk is equal to the scan radius R given by $$R = r_s \sin \delta \quad (8)$$

where $r_s$ is the distance from source to isocenter and $\delta$ is half the fan angle given by $$\delta = \frac{\Delta_\gamma N_d}{2} \quad (9)$$

where $\Delta_\gamma$ is the angle between detectors in a given row. The full detector width in the z-direction at isocenter is given by $$D = \omega_r N_r (r_s/r_d) \quad (10)$$

where $r_d$ is the distance from the source to the detector. We define the pitch, p, as the ratio of the table translation in 360 degrees of gantry rotation to D. Namely, $$p = \frac{s_t T}{D} \quad (11)$$

where $s_t$ is the table speed and T is the gantry rotation period. For example, for a pitch of one, the table moves a distance D in one rotation.

The simulation can use the same geometry of the scanner. Alternatively, the simulation can use more detector rows to improve the resolution in determining the z-interpolation table. See Table 1.

TABLE 1

| Parameter values and definitions. | |
|---|---|
| $N_d$ | Number of detector channels per row |
| $N_r$ | Number of rows |
| $N_h$ | Number of half scan views per image |
| $N_v$ | Number views per rotation |
| $N_m$ | Number of rows in simulation |
| $\Delta_\beta$ | Number of degrees per view |
| $\Delta_\gamma$ | Angle between detector channels in a row |
| $\Delta_{vj}$ | Slice separation in views |
| D | Full width of detector array at isocenter in z |
| R | Scan radius |
| $W_d$ | Distance between detector channels in q |
| $W_r$ | Distance between detector rows in z |
| $W_{diso}$ | Distance between detector channels in q at isocenter |
| $W_m$ | Distance between detector rows in z used in simulation |
| $r_s$ | Distance from source to isocenter |
| $r_d$ | Distance from source to center of detector array |
| $s_t$ | Table velocity |
| T | Gantry rotation period |
| p | Pitch |
| $\theta$ | Tilt angle |

As mentioned above, the interpolation line is determined by computing the centroid in the row direction of the resultant projection data. Let m be the simulation row index where $$0 \leq m < N_m \quad (12)$$

The interpolation point $m'[v,d]$, is given by calculating the centroid as follows:

$$m'[v,d] = \frac{\sum_{m=0}^{N_m-1} m C[v,m,d]}{\sum_{m=0}^{N_m-1} C[v,m,d]} \quad (13)$$

The value of $m'[v,d]$ is then converted into the true detector row variable $r'[v,d]$ where $(0 \leq r' < N_r)$. The $z'$-location of $m'$ is given by $$z' = (m' - m_c) \omega_m \quad (14)$$

where $m_c$ is the row location of $z'=0$ and $\omega_m$ is the distance between detectors in a given row in the simulation. The value of $r'$ is then obtained by substituting Equation (14) into Equation (3) for $z'$ and solving for r, which gives $$r'[v, d] = \frac{w_m}{w_r} (m'[v, d] - m_c) \quad (15)$$

The z-interpolation table is a function of the tilt angle, the geometry of the scanner, and the pitch. The pitch is fixed by the table speed, the gantry rotational speed, and detector size per Equation (11). The tilt angle can be chosen by a method described below.

Let the range of views from the scanner be given by $$0 \leq v < \infty \quad (16)$$

A slice is reconstructed by using a set of $N_h$ views. To reconstruct a series of adjacent slices, Steps 1 through 3 above are repeated for a different set of $N_h$ views for each slice. Let j be the slice number in the series of $N_j$ slices, $0 \leq j < N_j$. Also let $v_{oj}$ be the first view for a given slice j such that a given slice j uses the views $v_{oj} \leq v < v_{oj} + N_h$.

$$v_{oj} = j\Delta_{vj} \quad (17)$$

where $\Delta_{vj}$ is the separation in views between adjacent slices. The fan data for slice j are extracted from the cone beam data as follows:

$$F[v_h, d] = C[v_j, r'[v_h, d], d] \quad (18)$$

where $$v_j = v_h + v_{oj} \quad (19)$$

and where $0 \leq v_h < N_h$. Note that the z-interpolation table can be the same for each slice.

The plane of a tilted slice can be described by two rotations. The first rotation is about the x-axis by an angle $\theta$ and the second rotation is about the z-axis by an angle $\phi$. The equation of the nutated plane is given by $$x \sin\phi\sin\theta + y \cos\phi\sin\theta + (z - z_0) \cos\theta = 0 \quad (20)$$

where $z_0$ is the location of the center of the plane in z (i.e., in FIG. 6, $z_0 = 0$).

Figure 1:
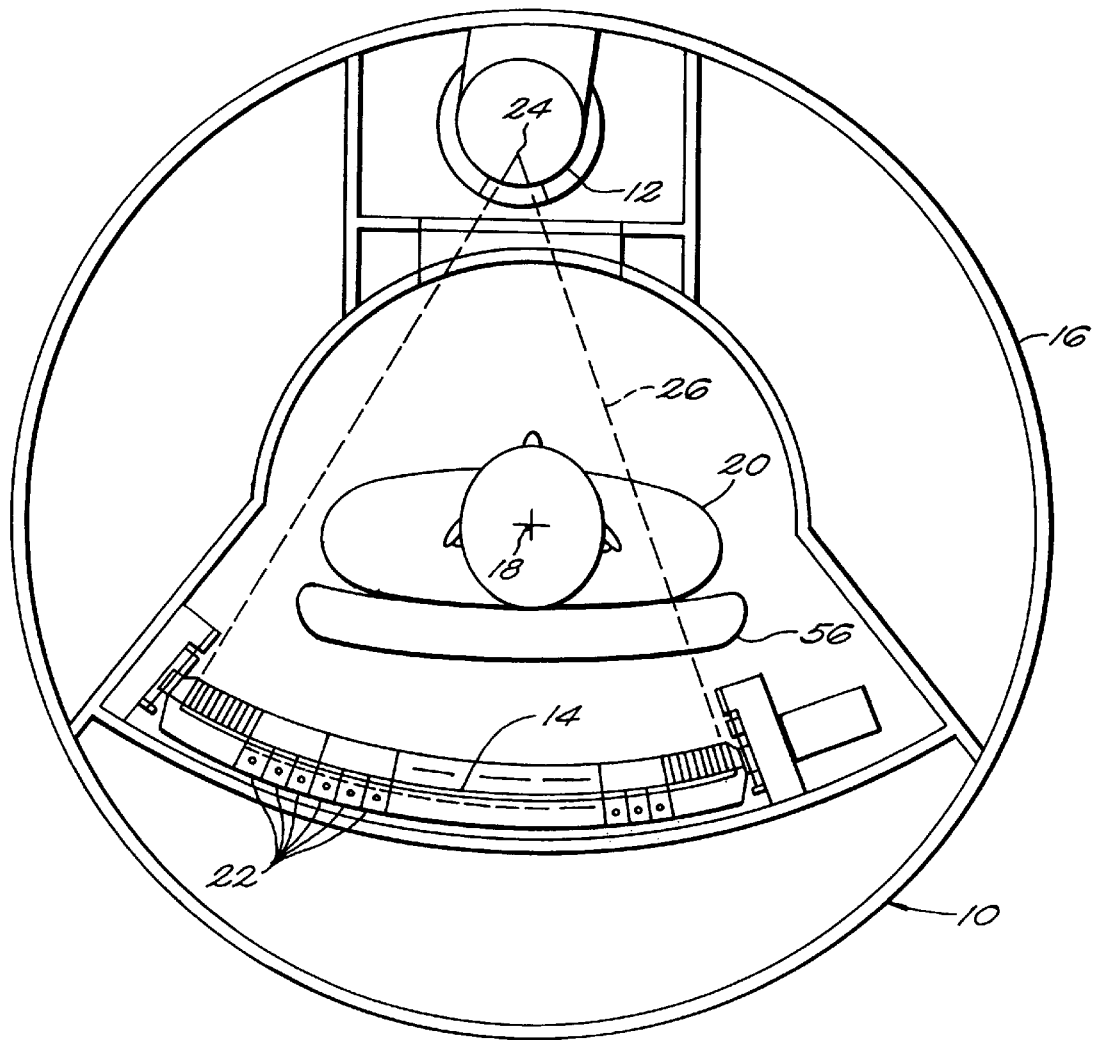
FIG. 1. is a schematic axial view of a typical conventional computed tomography (CT) scanner.
Figure 2:
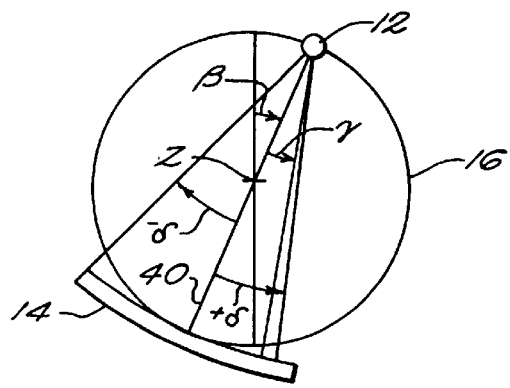
FIG. 2 is a schematic diagram which illustrates the projection angle and the detector angle of a CT scanning system.
Figure 3A:
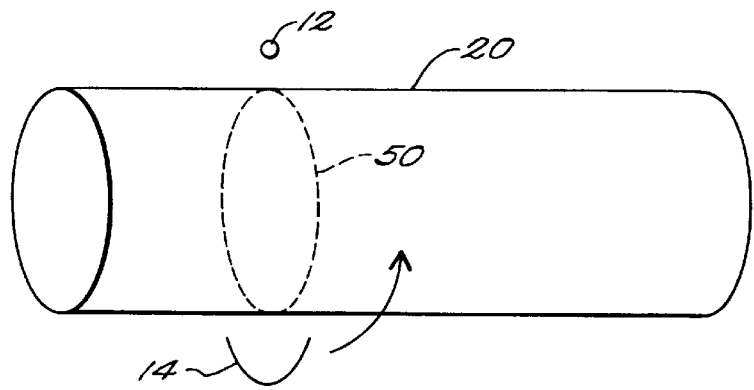
FIG. 3A illustrates the scanning path for a constant z-axis (CZA) scanning mode in a CT scanner.
Figure 3B:
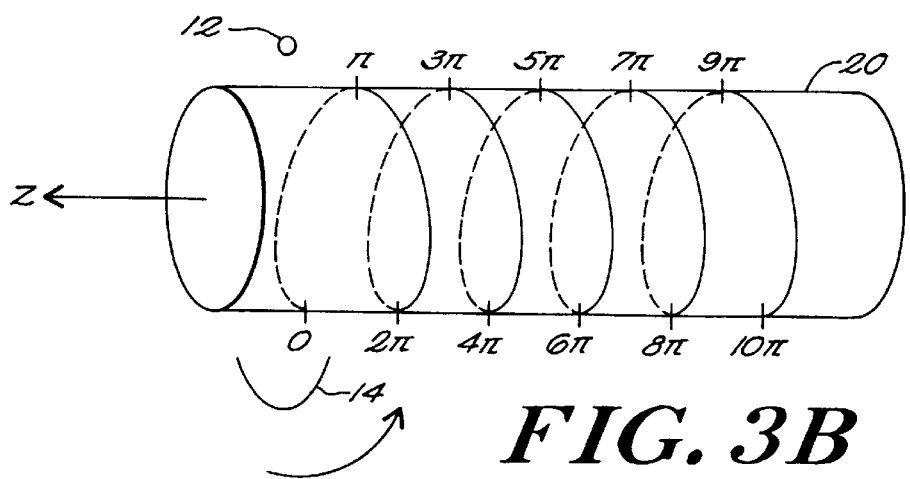
FIG. 3B illustrates the scanning path for constant-speed-helical (CSH) scanning in a CT scanner.

In a series of slices, the precession angle, $\phi$, is related to the view angle $\beta$. Let the gantry angle corresponding to $v_{oj}$ be denoted as $\beta_{oj}$. The precession angle for slice j is given by $$\phi_j = \beta_{oj} + \delta - \frac{\pi}{2} \quad (21)$$

where $\delta$ is half the fan angle as shown in FIG. 2 and defined in Equation (9).

The nutated slice geometry causes the slice separation in z to be a function of the location in x and y, as well as the pitch. At the center, (x,y)=(0,0), the location in z is given by $$z_{of} = \left( j - \frac{N_j - 1}{2} \right) \Delta_{z0} \quad (22)$$

where $\Delta_{zO}$ is the separation of slices at isocenter given by $$\Delta_{z0} = \Delta_{vj} \left( \frac{s_t T}{N_v} \right) \quad (23)$$

where $N_v$ is the number of views per rotation. In general, the separation at any point (x,y) is obtained by solving Equation (20) for z for two adjacent slice and taking the difference, namely, $$\Delta_{zj} = z_j - z_{j-1} \quad (24)$$

Figure 12:
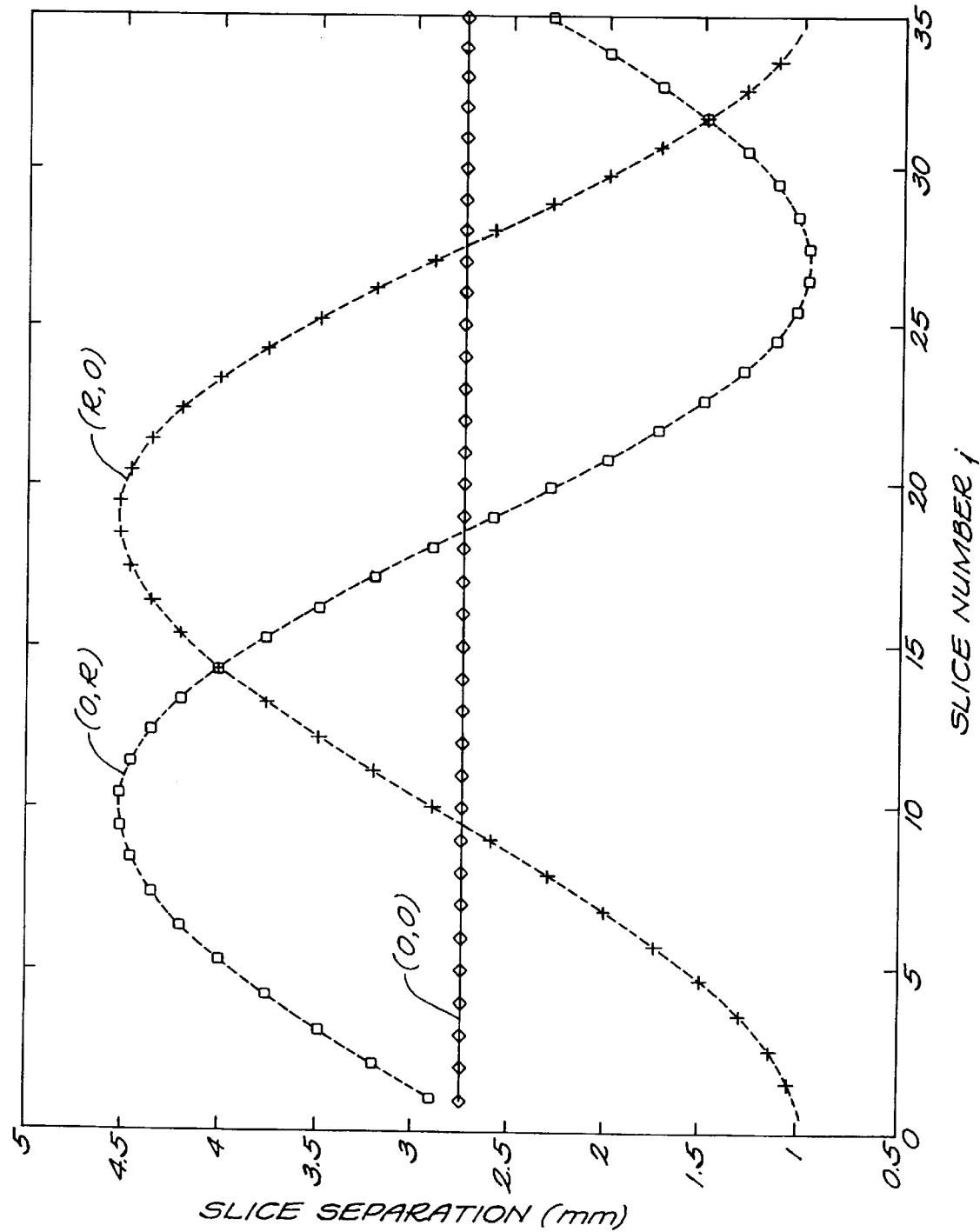
FIG. 12 is a schematic plot which shows slice separation in the z-axis direction in accordance with the present invention.

$\Delta_{zj}$ is sinusoidal, and oscillates about the nominal separation at isocenter which is a constant. FIG. 12 shows the slice separation for pixels located at (x,y)=(0,0), (R,0), and (0,R) where R is the scan radius. Each point on the curve represents a different slice in a series of 36 slices. The slices are separated by 10 views. The curves for (R,0) and (0,R) give the maximum amplitude. Pixels within R will give a smaller amplitude in the slice separation.

Once the fan-beam projection data are selected for a given tilted slice, it can be rebinned to parallel beam projection data. One rebinning procedure for continuous variables is disclosed in U.S. Pat. No. Re 30,947, which is incorporated herein by reference. Here we will describe the rebinning in terms of the discrete data.

Consider rebinning the fan data to 180 degrees of parallel data. As stated previously, the fan views needed to form 180 degrees of parallel views is equal to the number of fan views contained in 180+2δ degrees of gantry rotation. If an over-scan correction is used, more fan views are needed as discussed below. However, the rebinning procedure is the same with or without overscan.

The rebinning can be done in two steps by separating the radial (q-direction) and tangential (v-direction) interpolations. The relation between fan and parallel views is given by $$\beta_p = \beta_f + \gamma_f \quad (25)$$

where $\beta_p$ is the parallel view angle, $\beta_f$ is the fan view angle, and $\gamma_f$ is the fan detector angle. Let $v_p$ be the parallel view index, $(0 \leq v_p < N_p)$, and $v_f$ be the fan view index $(0 \leq v_f < N_h)$. The parallel view angle is given by $$\beta_p[v_p] = v_p \Delta_\beta + \delta \quad (26)$$

where $\Delta_\beta$ is the view angle spacing and $\delta$ is half the fan angle. For each parallel view and fan detector $d_f$, the interpolation point in fan view is calculated, $$v'_f = \frac{1}{\Delta_\beta} (\beta_p[v_p] - \gamma[d_f]) \quad (27)$$

where $\gamma[d_f]$ is the fan detector angle given by $$\gamma[d_f] = \Delta_\gamma (d_f - d_{cf}) \quad (28)$$

and where $d_{cf}$ is the center fan detector. A hybrid parallel projection, $P_h[v_p, d_f]$, is obtained with interpolation in the fan view direction $$P_h[v_p, d_f] = F[v'_f, d_f] \quad (29)$$

The radial interpolation is done as follows. Let t be the location of the desired equi-spaced parallel detectors.

$$t[d_p] = \omega_{diso}(d_p - d_{cp}) \quad (30)$$

where $\omega_{diso}$ is the detector channel spacing (in q) at isocenter, $d_p$ is the parallel detector channel number, $(0 \leq d_p < M_p)$, and $d_{cp}$ is the center parallel detector. The number of parallel detectors per view is given by $$M_p = \frac{2R}{w_{diso}} \quad (31)$$

The location of t in the fan detector array is given by $$d'_f[d_p] = \sin^{-1}\left( \frac{t[d_p]}{R} \right) \quad (32)$$

The parallel projection $P[v_p, d_p]$ is obtained by interpolating the hybrid projection data in the $d_f$, $$P[v_p, d_p] = P_h[v_p, d'_f] \quad (33)$$

The combination of the z-interpolation and rebinning consists of interpolation of the cone beam data in all three directions, i.e., $v_p$, d, and r. The z-interpolation can be done first, or it can be inserted into the rebinning procedure.

In stationary CT, parallel views should be symmetric over a range of 180 degrees. That is, a view taken at 0 degrees and a view at 180 degrees should contain the same information in the absence of motion due to symmetry. Object (or patient) motion destroys this symmetry and causes a discontinuity in the projection data for views separated by 180 degrees. This discontinuity results in artifacts in the reconstructed image which lead to the development of correction schemes such as the correction scheme described in U.S. Pat. No. 4,580,219, incorporated herein by reference.

Overscan correction is a method to smooth the discontinuity and decrease motion artifacts. This is accomplished by measuring extra views and weighting them before convolving and backprojecting. The number of extra views is usually small compared to the total number of views contained in $\pi$. Let the number of extra views be $N_{os}$ such that the parallel view data set is given by $0 \leq v_{os} < N_{pos}$, where $N_{pos} = N_p + N_{os}$. The data are first multiplied by weights to give weighted data $$P_\omega[v_{os}, d_p] = \omega[v_{os}] P[v_{os}, d_p] \quad (34)$$

where the weight $\omega$ is given by $$w[v_{os}] = \begin{cases} 3x_1^2 - 2x_1^3 & v_{os} < N_{os} \\ 1 - 3x_2^2 - 2x_2^3 & v_{os} \geq N_p \\ 1 & \text{elsewhere} \end{cases} \quad (35)$$

and where $$x_1 = \frac{v_{os} + 1/2}{N_{os}} \quad (36)$$

$$x_2 = \frac{v_{os} + 1/2 - N_p}{N_{os}} \quad (37)$$

After the weighted data are defined, there are at least two ways to proceed. Let $P_{out}$ be the output parallel projections that are convolved and backprojected. In the first method, the output projections are equal to the weighted projections, namely $$P_{out}[v_{os}, d_p] = P_\omega[v_{os}, d_p] \quad (38)$$

and the number of views is $N_{pos}$. In the second method, the output projections are given by $$P_{out}[v_p, d_p] = \begin{cases} P_w[v_{os} - N_p, d'_p] + P_w[v_{os}, d_p] & v_{os} \geq N_p \\ P_w[v_{os}, d_p] & \text{elserwhere} \end{cases} \quad (39)$$

where $$d' = M_p - 1 - d \quad (40)$$

and where $0 \leq v_{os} < N_p$. The second method has less output views than the first method. At first it may seem advantageous to backproject less views for computational efficiency. However, in a pipelined architecture the first method may be more efficient. This is because in the second method two views separated by $N_p$ are added together. It may not be possible in a pipeline to save a view in order to add it to another view that is acquired at a later time. Both methods will produce the same final image.

As described above, each nutated slice used to produce images in accordance with the invention is reconstructed from projection data taken at a plurality of projection or view angles. In one embodiment, to obtain sufficient data to fully reconstruct the slice, 240 total projections or views are taken at 240°, one projection or view for every degree. In one embodiment, data for successive slices are separated by 12°, resulting in an overlap between adjacent slices of 228 projections. As described above, each projection taken at each view can be considered a fan-beam projection which, in one embodiment of the present invention, is rebinned to parallel-ray data before it is reconstructed into image data for the slice.

The present invention also makes use of this rebinned projection data to create a projection image of the region being scanned from a single angle. This two-dimensional projection image is similar to what would be obtained if the region were to be scanned by the source and detector with the source and detector rotationally stationary while translated along the longitudinal axis of the region. This is also similar to the image obtained by a stationary x-ray line scanner which obtains image data from only a single angle through the region being scanned.

In the present invention, the projection image can be generated from the rebinned parallel-ray data obtained from the projection data gathered during scanning which, as described above, can be performed helically as the source and detector rotate about the object and translate along the object. In the present invention, a projection angle for the two-dimensional projection image is selected. For example, it may be desired to produce a projection image of the region from top to bottom, i.e., looking vertically into the region. In that case, the projection angle selected would be 0°. In another embodiment, it may be desirable to look at the object from the side. Accordingly, the selected projection angle would be 90°. In another situation, it may be desirable to view the region from several different angles. In that case, multiple projection angles can be selected, for example, 0°, 120° and 240°, such that the region can be viewed from evenly-spaced angles.

Given the selected projection angle, data are selected from the rebinned fan beam projections to generate the two-dimensional image. In one embodiment, for each slice, a single projection or view taken from a single corresponding view angle is selected. The selected view angle for a slice is the angle which corresponds to the projection angle selected for the projection image. It can be seen that for successive slices, the view used in the projection image is different. For example, as in the described embodiment of the present invention, where adjacent slices are separated by 12 views, the rebinned view data selected for adjacent slices, corresponding to the same preselected projection angle, will be offset by 12 views. That is, for example, within one slice, if the view corresponding to the selected projection angle is the 30th view, then the view selected from the next adjacent slice would be the 18th view. After a view is identified and selected for each slice to be used for the projection image, the selected view data are combined to generate the two-dimensional image of the region from the selected projection angle.

One prior approach to acquiring a projective image in CT is to scan the object with no gantry rotation while translating the object through the gantry. In the present invention, projective images are extracted from nutated slice projections obtained while the gantry is rotated. To illustrate, let each slice be separated by a constant incremental angle. Accordingly, corresponding view angles in adjacent slices can be regarded as being separated from each other by a constant $\Delta v$ views. For example, in one embodiment, $\Delta v=12$ views. The first view angle in each slice is separated from the first view angle in adjacent slices by $\Delta v$ views; the second view angle in each slice is separated from the second view angle in adjacent slices by $\Delta v$ views; etc. Let the first parallel projection be located at a view $v_0$. In the next slice, a parallel projection at $v_0+\Delta v$ is selected. This process continues for any desired length, i.e., any number of slices, or until there are no more slices. The result of combining the selected views is a parallel projective image at a fixed view angle. It should be noted that the projective image is nutated since the data are selected from nutated projection data. The final projective image can be interpolated to parallel if desired.

Each slice can be considered to be formed from an integer number N of views $v_i$, where i=1, . . . , N. In one embodiment, N=240, as described above. For each slice j, there exists a view $v_{ij}$ which contains the data corresponding to the preselected projection angle, and for the next adjacent slice, j+1, there exists a view $v_{i+\Delta v,\ j+1}$ which contains the data for the slice j+1 that corresponds to the preselected projection angle. Hence, the view $v_{j+1}$ selected from the next adjacent slice j+1 is given by $v_{j+1}=v_{i+\Delta v}$.

Figure 14:
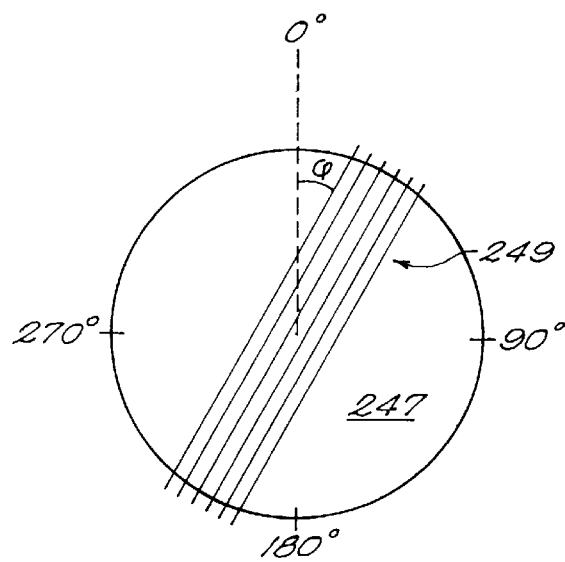
FIG. 14 is a schematic illustration which illustrates generating a two-dimensional projection image in accordance with the present invention.

FIG. 14 pictorially illustrates generation of the two-dimensional image projection of the invention. In one embodiment, the views for the projective image are selected from data that have been rebinned to parallel geometry. As shown in the figure, rebinned parallel data for each view in the image projection effectively include a series of parallel lines or samples 249 at the projection angle. In this case, the selected projection angle $\phi$ is selected to be 30°, that is, it is desired to produce a two-dimensional image of the scanning region 247 looking through the region at an angle of 30°. Therefore, for each slice generated in accordance with the foregoing description, there is a single projection or view, comprising a set of rebinned parallel data 249, taken from a corresponding view angle which would provide the data for the 30° view through the region. In the embodiment described herein, assuming that the slices start at 0°, for the first slice, the 30th view is selected since that view provides the data corresponding to the 30° projection through the region. For the second slice, the 18th view is selected. For the third slice, the 6th view is selected. For the next slice, the 174th view is selected. This accounts for the fact that, instead of acquiring a full 360° of data for each slice, only 180° plus twice the fan angle, or 240°, of data are obtained. Therefore, scan data for rays passing through the region in the opposite direction to that of the immediately proceeding slice are used. In addition, because the detector array is flipped 180° relative to the previous slice due to rotation about the center axis 18, the order of detector data in the selected projection must also be flipped, i.e., $d_i=d_{N-i}$, where d represents the data from a detector i, and N is the number of detectors in a view.

This process can continue through all of the slices of data, or as many slices as are needed, until a projection that corresponds to the preselected projection angle of 30° is identified for each slice to be used in the projection image. The data are then combined to generate the projection looking through the region at the preselected 30° angle. It will be understood that all of the slices need not be used to generate the image. To increase throughput, slices can be omitted from the projection angle, and the appropriate adjustment can be made to $\Delta v$.

Since the data used to generate these projections are already gathered by the initial scan, the data can be processed to produce projections from any angle. Additionally, multiple angles can be selected. This can be useful where it is desirable to view the region from different angles to identify suspect objects in the region. For example, it may be difficult to identify a prohibited item such as a hand gun using a view from only a single angle. However, where multiple projections are produced, the hand gun can be more readily identified. Hence, the projection image processing can be used as a pre-screening process to identify suspect bags in a baggage scanner. The image data for the suspect baggage can then be completely reconstructed to generate a full three-dimensional image of the baggage, if required.

In the CT scanning system of the invention, and in other conventional systems, each slice defines a set of image volume elements or "voxels." In traditional CT systems, these voxels are oriented with their axes parallel to corresponding coordinate axes in the field of view in the CT system. However, in the system of the present invention, as described above, the slices are nutated or tilted so that the volume elements are tilted with respect to the axes of the CT scanning region.

One application for the CT scanning system of the invention is in a commercial airport baggage scanner, as described above. One capability of the baggage scanner of the invention is identification of target substances such as explosives by analyzing scan data of the substance acquired by the system. One approach to identifying explosives is to compare the image density value for the substance obtained by the scanning system to known densities of known explosive materials. Densities within a predetermined tolerance of the known explosive density are concluded to be explosives. Further examination can then be performed to further analyze the item.

An important factor in scanning for explosives and determining the potential danger they present is the total mass of the explosive. In the present invention, the total mass can be computed by multiplying each density value of each voxel related to an explosive by its volume. The individual voxel masses from the voxels having densities which are identified as possibly being explosive densities are summed to determine the total mass of the explosive.

As noted above, in the NSR system, the voxels are tilted with respect to the scanning axis of the system. This results in slight errors when calculating the mass associated with a voxel. In the present invention, titled voxels can be interpolated to non-tilted density values, or, a correction factor can be computed to compensate for the tilt in the voxel. Either approach provides the ability to more accurately determine the total mass of a suspect object. Detailed descriptions of these approaches follow.

Figure 13:
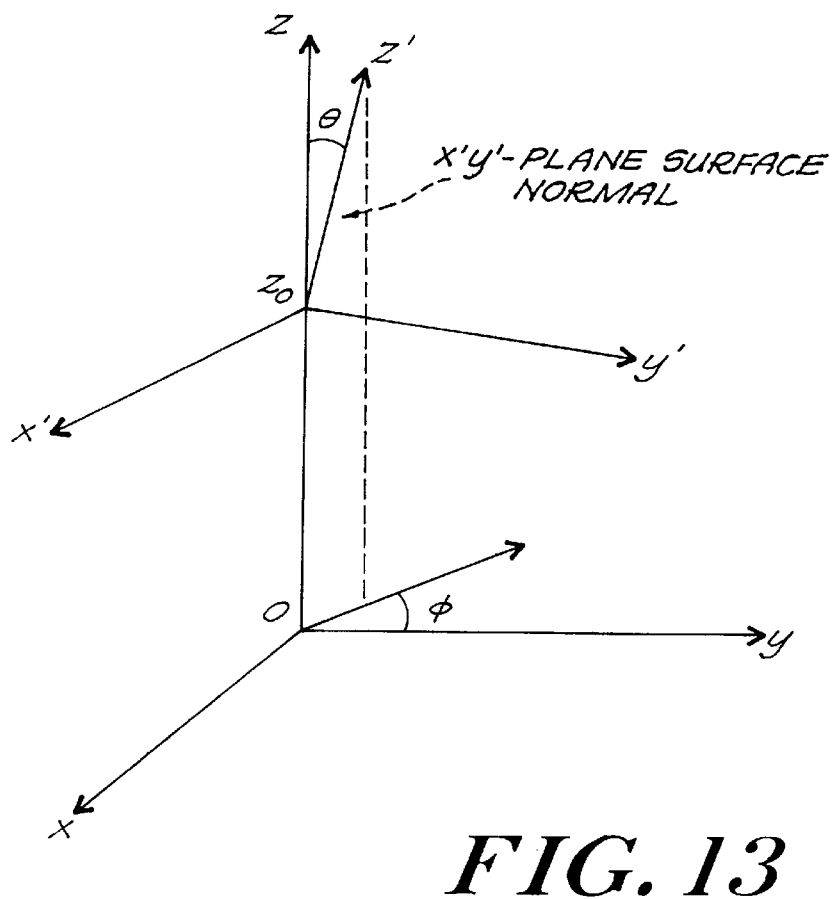
FIG. 13 is a graphical illustration of the relationship between the frames of reference for an object being scanned and the nutated image data slices generated in accordance with the present invention.

The frames of reference of the object being scanned and the nutated CT slices reconstructed by NSR are illustrated graphically in FIG. 13. The fixed frame of reference, on which the object is defined, is the xyz-space, and the frame of reference for the titled slices is defined by the x'y'-axes. The origin of the titled slice is at $z_0$. The nutation angle is $\theta$ and the precession angle is $\phi$. The nutation angle is amplified in this figure to emphasize the nutation and tilting of the reconstructed slices. In practice, the nutation angle can be small enough so that $\cos\theta\approx 1$ and $\sin\theta\approx 0$.

Let f(x,y,z) be the continuous object function that is to be reconstructed. The spatial extent of the object function is $|X^2+y^2|<R$, and $|z|<\infty$, where R is the scan radius. The scanner rotates about the z-axis. For the purpose of this description, it is assumed that the scanner also translates along the z axis while it is also rotating. The object can actually be translated instead of the scanner.

With NSR, a series of two-dimensional (2D) slices are reconstructed. The coordinate system of the 2D slices is the x'y'-plane, where the origin of this space is along the z-axis at $z_0$ as shown in FIG. 13. The 2D slices are nutated from the z-axis by θ. Note that the nutation takes place about the origin, $z_0$. The precession angle of the nutation is given by φ, where φ is measured with respect to the x-axis. The nutation is performed about a new x-axis that is formed by rotating about the z-axis by φ.

Let $f'(x',y';z_0)$ be a slice of the continuous object function in the nutated space at $z_0$. The relationship between the slices in their x'y'-plane and the xyz-space can be determined by rotating coordinate systems. Specifically, using a rotation matrix which includes the product of a first rotation by φ about the z-axis, followed by a second rotation by θ about the new x-axis, and finally followed by a rotation of ψ=−φ about the new z-axis. These three rotations are denoted $R_z(\phi)$, $R_x(\theta)$, $R_z(\psi)$, respectively. The rotations are given by the matrices $$R_z(\phi) = \begin{bmatrix} \cos\phi & \sin\phi & 0 \\ -\sin\phi & \cos\phi & 0 \\ 0 & 0 & 1 \end{bmatrix} \quad (41)$$

$$R_x(\theta) = \begin{bmatrix} 1 & 0 & 0 \\ 0 & \cos\theta & \sin\theta \\ 0 & -\sin\theta & \cos\theta \end{bmatrix} \quad (42)$$

$$R_z(\psi) = \begin{bmatrix} \cos\psi & \sin\psi & 0 \\ -\sin\psi & \cos\psi & 0 \\ 0 & 0 & 1 \end{bmatrix}. \quad (43)$$

The product of these three rotations, B, is given by $$B = \begin{bmatrix} \cos\psi\cos\phi & \cos\phi\sin\psi & \sin\phi\sin\theta \\ -\sin\psi\cos\theta\sin\phi & +\sin\phi\cos\theta\cos\psi & \\ -\sin\phi\cos\psi & -\sin\phi\sin\psi & \cos\phi\sin\theta \\ -\cos\phi\cos\theta\sin\psi & +\cos\phi\cos\theta\cos\psi & \\ \sin\theta\sin\psi & -\sin\theta\cos\psi & \cos\theta \end{bmatrix} \quad (44)$$

In practice, θ can be sufficiently small so that cos θ≈1. Using this approximation and the relation that ψ=−φ, equation (44) reduces to $$B = \begin{bmatrix} 1 & 0 & \sin\phi\sin\theta \\ 0 & 1 & \cos\phi\sin\theta \\ -\sin\theta\sin\phi & \sin\theta\cos\phi & 1 \end{bmatrix} \quad (45)$$

The relationship between the reference frames is given by the following equation:

$$\begin{bmatrix} x \\ y \\ z \end{bmatrix} = B \begin{bmatrix} x' \\ y' \\ 0 \end{bmatrix} + \begin{bmatrix} 0 \\ 0 \\ z_0 \end{bmatrix} = \begin{bmatrix} x' \\ y' \\ -x'\sin\theta\sin\phi + y'\sin\theta\cos\phi + z_0 \end{bmatrix}. \quad (46)$$

Equation (46) says that the x'- and y'-axes map directly into the x- and y-axes, respectively. However, the z-axis is compressed or expanded depending on the x'-y' position, the precession angle, φ, and the nutation angle, θ. It follows that $$f'(x',y';z_0)=f(x, y, z) \quad (47)$$

per the transformation given in (46). It should be noted that the relationship between the x'y'- and xyz- coordinate systems changes for each reconstructed slice, which is denoted by its $z_0$ value.

Sampling of coordinates and the interpolation used to generate parallel slices are now described. Assume that an infinite set of parallel slices is desired, where each slice is composed of N×N pixels. The slices are spaced by $\delta_z$ along the z-axis. Let k be the index, or slice number, of the parallel slices, where −∞<k<∞. Let i and j be the sample indices along the x- and y-axes, respectively, where 0≤i<N and 0≤j<N. Let the sampled slices be denoted F(i,j,k). The sampled and continuous functions can be related as follows:

$$F(i,j,k)=f(x,y,z) \quad (48)$$

for $$x=-R+(i+½)\delta_{xy}$$

$$y=R-(j+½)\delta_{xy}$$

$$z=k\delta_z \quad (49)$$

where the pixel size, $\delta_{xy}$, is 2R/N. Note that other definitions for x and y can be used. For example, the pixel size can be defined as $\delta_{xy}$=2R/(N−1), or a reconstruction field-of-view smaller than the scan field-of-view, 2R, can be used.

Similar relationships can be written for images in the nutated space. The sampled nutated space is given by F(i',j',k'), where $$F'(i',j',k')=f'(x',y',z_0) \quad (50)$$

for $$x'=-R+(i'+½)\delta_{xy}$$

$$y'=R-(j'+½)\delta_{xy}$$

$$z=k'\delta_{z'} \quad (51)$$

where i', j' are the sample indices along the x'-, and y'-z' axes, respectively. The index k' is the sample index of the tilted slices corresponding to $z_0$. The ranges of the indices are 0≤i'<N, 0≤j'<N, and −∞<k'<∞. The parameter $\delta_{z'}$ is the z-axis spacing between the nutated slices and is generally not equal to $\delta_z$. Let $\phi_{k'}$ be the precession angle for each slice k', where $$\phi_{k'}=ck'+\phi_0 \quad (52)$$

and where $$c = \frac{2\pi\delta_{z'}}{z_r} \quad (53)$$

and finally where $z_r$ is the nonlinear distance per 2π of rotation, and $\phi_0$ is a phase offset to the precession angle determined by starting angle of the scanner. Without the loss of generality, assume that $\phi_0$=0. The variable M is used to describe the number of images per rotation; this is given by $$M = \frac{z_r}{\delta_{z'}}. \quad (54)$$

It now follows that $$F(i, j, k)=F'(i', j', k') \quad (55)$$

for $$i'=i \quad (56)$$

$$j'=j \quad (57)$$

and $$k'=g^{-1}(i, j, k) \quad (58)$$

where $$k = g(i, j, k') = \frac{-x'\sin\theta\sin(ck') + y'\sin\theta\cos(ck') + k'\delta_z}{\delta_z} \quad (59)$$

where x' and y' are given in (51). The last equation, (59), is nonlinear in k'. The equation can be solved using numerical techniques such as Newton-Raphson. Alternatively, the values of g(i j, k') for the given values of k' can be tabulated for each value of i and j. The values can be searched to determine the values of k' that bracket a desired value of k. In practice, k' may not be an integer and (55) is replaced with interpolation between adjacent values of k'. Linear interpolation can be used.

After compensation for nutation, the collection of slices is denoted by F (i, j, k), where i and j correspond to sampling in the imaging plane (i.e., the xy-plane) and k corresponds to sampling in the axial direction (i.e., the z-direction). The in-plane pixel size is $\delta_{xy}$. The axial sampling distance is $\delta_z$. Therefore, the volume of each voxel is $\delta^2_{xy}\delta_z$. Assuming that the function F (i, j, k) represents the density of the object, then the mass of the voxel located at (i, j, k) is $\delta^2_{xy}\delta_z F$ (i, j, k).

It is an object of explosive detection to determine the mass of potential explosives in a scanned object. A procedure for determining which voxels are part of an explosive is implemented. A typical method for this procedure is connected components labeling (CCL). The output of this procedure is a binary "window" function, W (i, j, k), indicating if the voxel located at (i, j, k) is part of an explosive. Therefore, $$W(i, j, k) = \begin{cases} 1; & \text{if voxel at } (i, j, k) \text{ is an explosive} \\ 0; & \text{elsewhere.} \end{cases} \quad (60)$$

The mass of the explosive, $M_e$, is given by $$M_e = \delta^2_{xy}\delta_z \sum_i \sum_j \sum_k F(i, j, k) W(i, j, k). \quad (61)$$

Now the case of nutated slices in accordance with the invention is considered. As described above, they are denoted F'(i', j', k'). The in-plane dimension is still given by $\delta_{xy}$. However, the axial positions of each slice, $z_{k'}$, are given by $$z_{k'} = -x'\sin\theta\sin(ck') - y'\sin\theta\cos(ck') + k'\delta_z \quad (62)$$

where x', y', and c are defined above. The axial extent of the voxel located at (i', j', k'), $\Delta_{k'}$, is approximated with $$\Delta_{k'} = \frac{z_{k'+1} - z_{k'-1}}{2}. \quad (63)$$

The same procedure for determining which voxels are part of an explosive used for the parallel slices can be used on the nutated slices. Therefore, CCL might be used. The output of this procedure is a binary window function, W'(i', j', k'), indicating if the voxel located at (i', j', k') is part of an explosive. The mass of explosive can be determined using the following equation (64):

$$M_e = \delta^2_{xy} \sum_{i'} \sum_{j'} \sum_{k'} \Delta_{k'} F'(i', j', k') W'(i', j', k'). \quad (64)$$

One advantage of using (64) over (61) is that the interpolation between F'(i',j',k') and F(i, j, k) is eliminated. The interpolation increases partial volume artifacts that can lower the density values of thin explosives. This lowering, in turn, makes the task of determining which voxels are part of an explosive more difficult.

In another aspect of the invention, a parallel processing architecture is employed to generate and process the nutated image data slices of the invention to provide more efficient processing than would be obtained in a conventional pipeline processing system. The improved efficiency realized by the parallel processing architecture results in greatly improved image generation efficiency and therefore makes the system applicable to high-scanning-throughput settings such as in the airport baggage scanner of the invention.

Figure 15:
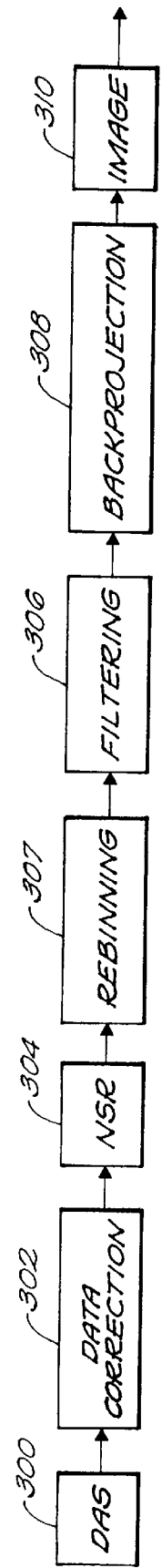
FIG. 15 is a schematic functional block diagram which illustrates generating and processing nutating slice data in accordance with the invention using a pipeline processing approach.

FIG. 15 contains a schematic functional block diagram of a serial pipeline approach to generation and processing of nutated slice data in accordance with the present invention. In this system, the data acquisition system (DAS) 300, which includes the radiation source and array of detectors, acquires the scan data and transfers them to a data correction process 302. The data correction process applies corrections to the data such as those required to compensate for air detector readings, detector temperature offsets, detector non-linearities, and general imperfections in the system. Following correction 302, the scan data are transferred to the nutating slice reconstruction data generation 304 which extracts the fan-beam projections from the sets of projection data in the scan data, as described above in detail. Next, the generated fan-beam projections can be applied to an optional rebinning process 307 to generate rebinned parallel-beam projections from the fan-beam projections. For each slice, the fan-beam or rebinned parallel-beam projections are transferred to a filtering process 306 which filters the projections and then to a backprojection process 308 which generates the image data for the slices. Finally, the slice image data are used to generate an image 310.

This pipeline approach suggests that slices are generated and backprojected one at a time from the scan data acquired by the DAS 300. However, in actuality, as described above, each set of projection data from each individual view is used to generate projections for multiple adjacent slices. This is due to the overlap of slice data in successive or adjacent views. In the embodiment described above, each slice is generated from scan data acquired at 240 discrete views. Therefore, for each slice, at each of 240 positions around the longitudinal axis, a single fan-beam projection is extracted from the full set of projection data acquired at that position. However, as described above, each slice is separated by only 12° of view rotation. As a result, there is considerable overlap of scan data over many slices. That is, the scan data acquired at one particular view angle are used to generate many slices. For example, in the embodiment described above, where each slice uses 240 views separated by 1° and slices are separated by 12° of rotation, each set of projection data at single view can be used in generating 20 slices. In actuality, due to effects at the ends of the data stream, each view actually contributes to 22 slices, in one embodiment.

As a result of this overlap, the NSR process 304 illustrated in FIG. 15 actually generates projections for many slices, e.g., 22, simultaneously. That is, instead of generating a single projection for a single slice at each of the 240 views, it actually generates 22 projections at each of the 240 views. This can be a heavy processing load in a pipeline processing configuration.

Figure 16:
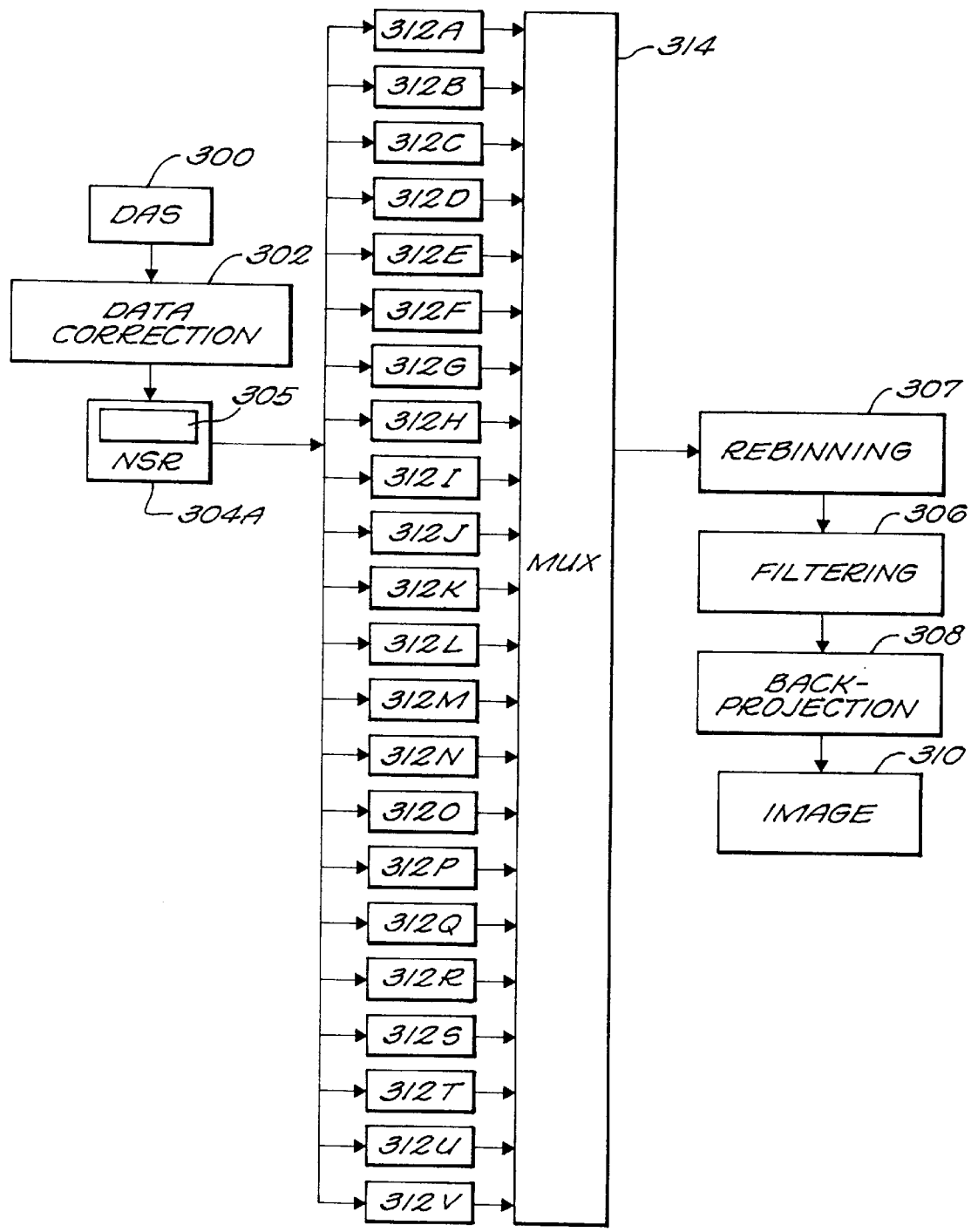
FIG. 16 is a schematic functional block diagram which illustrates generating and processing nutating slice data in accordance with the invention using a parallel memory processing approach with a single processor.

FIG. 16 is a schematic functional block diagram which illustrates a parallel configuration in accordance with the invention which can be used to generate and process the projections used to generate the nutated slices of the invention. Once again, a DAS 300 generates scan data which are corrected by a data correction process 302 before being forwarded to the NSR process 304A. In this configuration, the NSR process can be performed by a single processor 305 which analyzes the scan data to generate the fan-beam projections needed to generate the nutated slices. At each projection angle, the processor 305 generates a fan-beam projection for each slice to which the projection data under consideration contributes data. In general, as described above, each set of projection data will contribute to several slices, e.g., 22, and, therefore, several projections will be generated. In this embodiment of the invention, each slice being generated is associated with its own data storage element or memory 312. In the embodiment illustrated in FIG. 16, since each set of projection data may contribute to as many as 22 slices, there are 22 memories 312A–312V used to store generated projections.

At each view, the processor 305 generates a projection for each slice. The projection generated for a slice is forwarded to and stored in the memory element 312 associated with that slice. In general, where 22 slices are being generated simultaenously, 22 projections are generated from each view and are stored in 22 respective associated memories 312.

This process of generating projections and storing them in preassigned memories continues until all require data are processed. For every 240 views, a single slice is complete, i.e., all of the projections for a slice have been generated and stored in its respective associated memory. When the memory element 312 thus becomes full, the projections stored in the memory element, which are those required to generate the single slice, are forwarded to a mux 314 which selects the memory that is providing the slice projections. The full set of projections for the slice can then be transferred to an optional rebinning process 307 which can rebin the fan-beam projections to parallel-beam projections. Next, a filtering process 306 can be performed on the data and then backprojection 308 can be performed to generate image data for the nutated slice. After the slices are generated, an image 310 can be produced.

The process of filling the memories 312 with projections continues through all views at which scan data were acquired. Since slices are separated by 12 views in one embodiment, for every 12 views processed, one of the memories 312 becomes full with the required 240 projections for a slice. On the next view, the memory which was filled on the previous view begins being filled again with projections from another slice to be generated. Hence, where slices are separated by, for example, 12 views, generation of projections for a slice is completed every 12 views. Accordingly, every 12 views, a memory element 312 fills up. On the next view that memory element begins gather elements for a new slice.

This configuration allows slice projection data to be processed very efficiently. Projections are generated for multiple slices simultaneously, but the actual slices can be rebinned, filtered and backprojected one at a time.

Figure 17:
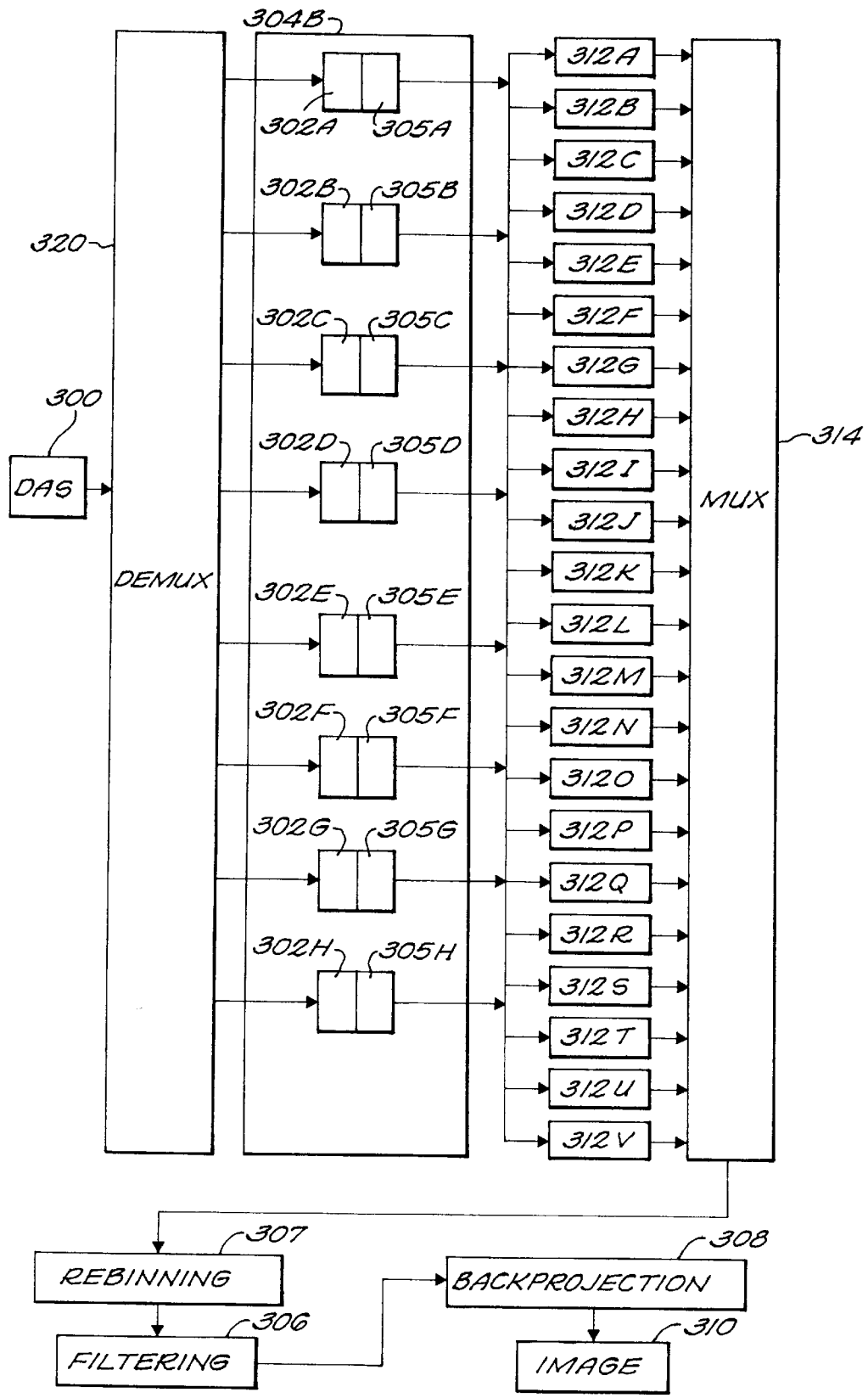
FIG. 17 is a schematic functional block diagram which illustrates generating and processing nutating slice data in accordance with the invention using a parallel memory approach with multiple parallel processors.

FIG. 17 is a schematic functional block diagram of another embodiment of the invention using a parallel configuration to generate and process the nutated slices of the invention. In the embodiment shown in FIG. 17, the parallel memories 312A–312V are used in the same fashion as described above in connection with FIG. 16 to store fan-beam projections for individual slices as they are generated. However, the configuration includes a multiple-processor stage 304B which includes multiple data correction stages 302A–302H coupled respectively to multiple NSR processing stages 305A–305H. Scan data are received from the DAS 300 by a demultiplexor circuit 320, which routes the data to a selected one of the 302/305 data correction and nutating slice processing stages. Each correction/nutating slice processing stage 302/305 receives data for a single view from the demux 320. It analyzes the set of projection data from the single view to generate fan-beam projections for each of the slices for which the particular view contributes projection data. The generated projections are then transferred to the memories 312 associated with the slices that use the generated projections. Again, in the example described herein, each view contributes a single projection to each of 22 slices and, therefore, the processor 305 transfers 22 projections to 22 memory elements 312A–312V for each view or set of projection data.

In the embodiment shown in FIG. 17, eight nutating slice correction/processing elements 302/305 are used. It will be understood that different numbers of processing elements can be used. The demux 320 cycles through the eight elements one at a time as the sets of projection data for each view are received from the DAS 300. This provides a level of parallelism to the scan data processing and therefore greatly increases the speed at which the processing can be performed. This is very helpful in settings such as the baggage scanner in which high scanning throughput is required.

As shown in FIG. 17, all of the nutating slice processing elements can transmit projections to any of the memory elements 312. In another embodiment, each processor can only communicate with a portion of the memory elements 312. This approach can be used to simplify communication between the processors 305 and the memories 312 and also to eliminate contention for the memories 312.

In one embodiment, a memory element 312 becomes full of projections for a slice when it contains 240 projections. The full set of projections is transferred via mux 314 to the optional rebinning process 307. After the fan-beam projections are rebinned to parallel-beam projections, they are filtered 306 and backprojected 308 into image slices. The slices can then be used to generate an image 310.

In one embodiment, the rebinning process 307 can be implemented on one of the processing elements 305. In that embodiment, when rebinning of data is required, one of the processors 305 is commanded to perform the rebinning. After a processor is commanded to perform rebinning, when that processor completes its present task of generating projections of a particular view, instead of processing the next view, it is temporarily interrupted so that it can perform the required rebinning function. When the rebinning process is completed, the processor rejoins the other processors in the projection data processing cycle. In one embodiment, any of the processors can be commanded to perform rebinning at any time. This approach to sharing a processor eliminates hardware complexity in the system by reducing the number of processors and associated circuitry in the system.

While this invention has been particularly shown and described with references to preferred embodiments thereof, it will be understood by those skilled in the art that various changes in form and details may be made therein without departing from the spirit and scope of the invention as defined by the following claims.

What is claimed is:

1. A method of generating a two-dimensional projection image of an object in a region having a longitudinal axis, said method comprising:
    scanning the region to generate scan data representative of the region, said scanning comprising:
        providing a radiation source and an array of detectors on opposed sides of the region,
        rotating at least the radiation source about the longitudinal axis while the radiation source emits radiation toward the array of detectors, and with the array of detectors, receiving radiation from the region to generate the scan data for the region;

defining a plurality of image data slices corresponding to a plurality of positions along the longitudinal axis of the region, successive image data slices being non-parallel with each other, each of said image data slices defining a plurality of scan data projections obtained from a respective plurality of view angles during the scanning step, each scan data projection containing scan data at its respective view angle;

selecting a projection angle for the two-dimensional projection image of the region;

for each of said image data slices, identifying the view angle that corresponds to the selected projection angle;

for each of said image data slices, selecting the scan data projection that corresponds to the identified view angle; and generating the two-dimensional projection image of the region using the selected scan data projections.

2. The method of claim 1 wherein the array of detectors is also rotated about the longitudinal axis to scan the region.

3. The method of claim 1 wherein scanning the region further comprises translating the object relative to the radiation source and the array of detectors along the longitudinal axis of the region while rotating at least the radiation source about the longitudinal axis of the region.

4. The method of claim 1 further comprising selecting a second projection angle for a second two-dimensional projection image of the object, said second two-dimensional projection image being generated from the scan data generated during the scanning step.

5. The method of claim 1 further comprising selecting a plurality of additional projection angles for a plurality of additional two-dimensional projection images of the object, said plurality of additional two-dimensional projection images being generated from the scan data generated during the scanning step.

6. The method of claim 1, wherein the region is scanned with a computed tomography (CT) device to generate the scan data.

7. The method of claim 1, wherein the radiation source is a cone-beam source.

8. The method of claim 1, wherein successive image data slices are nutated with respect to each other.

9. The method of claim 1, wherein the array of detectors is a two-dimensional array.

10. The method of claim 1, wherein the scan data is generated using a helical scan.

11. The method of claim 1, wherein the scan data is generated using a helical cone-beam scan.

12. The method of claim 1, further comprising rebinning the scan data to parallel-ray scan data.

13. The method of claim 1 wherein each image data slice defines a slice plane having a normal axis forming a tilt angle with the longitudinal axis of the region and a rotation angle with a transverse axis of the region transverse to the longitudinal axis, such that the normal axes of successive image data slices have the same tilt angle and different rotation angles.

14. An apparatus for generating a two-dimensional projection image of an object in a region having a longitudinal axis, said apparatus comprising:

a radiation source and an array of detectors on opposed sides of the region, said radiation source being mounted on a rotatable member rotatable about the longitudinal axis of the region while the radiation source emits radiation toward the array of detectors, said array of detectors receiving radiation from the region to generate scan data for the region;

means for defining a plurality of image data slices corresponding to a plurality of positions along the longitudinal axis of the region, successive image data slices being non-parallel with each other, each of said image data slices defining a plurality of scan data projections obtained from a respective plurality of view angles during the scanning step, each scan data projection containing scan data at its respective view angle;

means for selecting a projection angle for the two-dimensional projection image of the region;

means for identifying, for each of said image data slices, the view angle that corresponds to the selected projection angle;

means for selecting, for each of said image data slices, the scan data projection that corresponds to the identified view angle; and means for generating the two-dimensional projection image of the region using the selected scan data projections.

15. The apparatus of claim 14 wherein the array of detectors is also mounted on the rotatable member.

16. The apparatus of claim 14 further comprising means for translating the object relative to the radiation source and the array of detectors along the longitudinal axis of the region while the radiation source is rotated about the longitudinal axis of the region.

17. The apparatus of claim 14 further comprising means for selecting a second projection angle for a second two-dimensional projection image of the object, wherein the means for generating generates said second two-dimensional projection image from the scan data.

18. The apparatus of claim 14 further comprising means for selecting a plurality of additional projection angles for a plurality of additional two-dimensional projection images of the object, wherein the means for generating generates said plurality of additional two-dimensional projection images from the scan data.

19. The apparatus of claim 14 wherein the apparatus is a computed tomography (CT) system.

20. The apparatus of claim 14 wherein the radiation source is a cone-beam source.

21. The apparatus of claim 14 wherein the array of detectors is a two-dimensional array.

22. The apparatus of claim 14 further comprising means for rebinning the scan data to parallel-ray scan data.

* * * * *